US008404223B2

(12) United States Patent
Garnett et al.

(10) Patent No.: US 8,404,223 B2
(45) Date of Patent: Mar. 26, 2013

(54) POLYMER

(75) Inventors: Martin Garnett, Nottingham (GB); Paolo Ferruti, Milan (IT); Elisabetta Ranucci, Milan (IT)

(73) Assignees: The University of Nottingham, Nottingham (GB); The University of Milan, Milan (IT)

( * ) Notice: Subject to any disclaimer, the term of this patent is extended or adjusted under 35 U.S.C. 154(b) by 650 days.

(21) Appl. No.: 12/443,278

(22) PCT Filed: Sep. 14, 2007

(86) PCT No.: PCT/GB2007/050544
§ 371 (c)(1),
(2), (4) Date: Mar. 27, 2009

(87) PCT Pub. No.: WO2008/038038
PCT Pub. Date: Apr. 3, 2008

(65) Prior Publication Data
US 2010/0028445 A1 Feb. 4, 2010

(30) Foreign Application Priority Data

Sep. 29, 2006 (GB) .................................. 0619175.3

(51) Int. Cl.
*A61K 31/74* (2006.01)
(52) U.S. Cl. .................................................. 424/78.17
(58) Field of Classification Search .................. None
See application file for complete search history.

(56) References Cited

U.S. PATENT DOCUMENTS

| 5,606,012 | A | 2/1997 | Tanzi et al. | |
|---|---|---|---|---|
| 6,020,457 | A * | 2/2000 | Klimash et al. | 528/373 |
| 2005/0256032 | A1 * | 11/2005 | Mohanty et al. | 514/2 |
| 2009/0104254 | A1 * | 4/2009 | Sinko et al. | 424/450 |

FOREIGN PATENT DOCUMENTS

| WO | 93/21257 A1 | 10/1993 |
|---|---|---|
| WO | WO 0078285 A1 * | 12/2000 |

OTHER PUBLICATIONS

Search Report of corresponding PCT/GB2007/050544, 2007.
Ranucci et al, "Poly(amidoamine)s with potentional as drug carriers: degradation and cellular toxicity," Journal of Biomaterials Science 2(4):303-315 (1991).

* cited by examiner

*Primary Examiner* — Paul Dickinson
(74) *Attorney, Agent, or Firm* — LeClairRyan, a Professional Corporation

(57) ABSTRACT

The invention provides compositions comprising a polyamidoamine (PAA) polymer comprising a pendant disulphide, sulphydryl, or activated sulphydryl moiety, and methods for their manufacture. The invention extends to the use of such polyamidoamine polymers to form cross-linked compositions, and hydrogels comprising the same, and the use of such compositions in various biological and non-biological applications, such as the delivery of biomolecules to target sites, and for tracking fluid flows. The invention also provides carrier particles, which may be used to deliver biomolecules, and to methods of treatment. The invention also provides a fluid tracking system for monitoring fluid flow.

62 Claims, 16 Drawing Sheets

Scheme 1 PAA containing pendant sulphydryl moieties

Scheme 1 PAA containing pendant sulphydryl moieties

Scheme 2 - Cross-linkable PEG-PAAs to give multiblock linear PEG-PAA

Scheme 3 Cross-linkable PEG-PAA comb co-polymers

Scheme 4 PEG terminated PAA with Block of pendant sulphydryl groups

Scheme 5 Reaction scheme for preparing a polyamidoamine containing cystamine residues Scheme 6 Reaction scheme for reducing BOC protected cystamine containing polymers to give a free sulphydryl group Scheme 7 Reaction scheme for activating free sulphydryl groups by thiol disulphide interchange with bipyridyl disulphide Scheme 8 Reaction scheme for the formation of hydrogel by reaction of polymers containing a reduced thiol and polymers containing an activated thiol Scheme 9 Reaction scheme for reduction of hydrogels to their component polymers Scheme 10 – Syntheses of CP polymers precursors.

D) = A + C

E) = 2xD + B

Scheme 11 - General synthesis of CP polymers

Scheme 12 - Synthesis of XLP polymers.

Particle surface

ON FILTER

FILTRATE

General structure of CP polymers. CP03: a=16, b=15; CP04: a=16, b=48; CP05: a=45, b=48; CP06: a=45, b=15

POLYMER

This application is a national stage application under 35 U.S.C. §371 from PCT Application No. PCT/GB2007/050544, filed Sep. 14, 2007, which claims the priority benefit of Great Britain Application No. 0619175.3, filed Sep. 29, 2006.

The present invention relates to polymers, and in particular, to polyamidoamines, and methods for their manufacture. The invention extends to the use of such polyamidoamine polymers to form cross-linked compositions, and hydrogels, and the use of such compositions in various biological and non-biological applications, such as the delivery of biomolecules to target sites, and in fluid tracking systems Linear polyamidoamines (PAAs) are known polymers, which consist of a backbone chain having amido- and tertiary amino groups that are arranged regularly along the backbone. PAAs are positively charged (i.e. cationic) and are degradable in water because they contain hydrolysable amidic bonds in their backbone chain together with nucleophilic tertiary-aminic functions at their beta position. The polymers can be synthesised from a wide variety of primary monoamines or secondary bisamines, which enables full control to be exercised over the spacing and pKa of cationic groups along the backbone.

PAAs may be designed to have a range of useful physicochemical properties depending on which specific monomers or co-monomers are chosen, and also their position along the backbone. PAAs have been shown to have a relatively low biological toxicity in contrast to many other cationic polymers. In addition, the polymers are highly hydrophilic, and usually degrade in aqueous media at a rate depending on their structure. The combination of beneficial physicochemical properties and good biocompatibility make PAAs a suitable choice for their use in various biological applications.

Cationic polymers such as PAAs have potential applications in many areas due to their positive charge. Positively charged polymers have found use in the binding of various charged biological molecules for their purification (e.g. heparin binding), and also in the formation of polyelectrolyte complexes. The term "polyelectrolyte" is given to polymers whose repeat units bear an electrolyte group, which dissociate in aqueous solutions (e.g. water), thereby making the polymers charged. Charged polymers such as poly(D-lysine) and poly(L-lysine) (PLL) have been used as cell adhesion substrates for many years, but their toxicity makes them problematic for this purpose.

PAAs have also been used in various medical applications. For example, PAAs can act as useful polymers for the preparation of polyelectrolyte complexes for the delivery of biomolecule payloads, such as DNA constructs, to a target site in a patient. For example, in vitro, PAAs with a number of different combinations of co-monomers have exhibited good transfection activity for various biomolecule payloads. It is known that there are various physical barriers which make the delivery of a payload biomolecule, such as plasmid DNA, to the nucleus of cells, difficult. Such barriers include physiological media such as blood with high salt and protein contents, the initial uptake into the cell, avoiding degradation in the cell via the endosome/lysosome systems, transport through the cytoplasm to the nucleus, and crossing the nuclear membrane itself. Therefore, there is a need for the development of new PAA complexes, which exhibit improved delivery of payload biomolecules to the target site.

In addition to medical applications of PAAs, such as DNA delivery systems for use in patients, there are also considerable applications for the use of PAA complexes in the delivery and protection of active payload biomolecules in the environment. However, in many environmental applications, where the payload molecule may be exposed to extreme conditions, the stability of the PAA-biomolecule complex is an important consideration, and so it is vital that the complex is sufficiently stabilised for it to be effective. Furthermore, a significant problem with using PAAs in many applications is that the polymers have a tendency to aggregate and interact with charged surfaces, such as soils and minerals. Accordingly, in order to reduce aggregation and prevent interaction of the PAAs with such charged surfaces, sterically-stabilised PAA complexed with a PEGylated surface have been used. The PEGylation in high salt environments has been shown to increase stabilisation against unwanted aggregation of PAA complexes.

PAA complexes for use in such medical and environmental applications have also been developed with the incorporation of polyethylene glycol (PEG) block copolymers to increase the half-life of complexes circulating in the blood. Hence, methods have been developed to produce sterically-stabilised complexes incorporating PAAs and PEG. However, while the polyelectrolyte complexes that are produced by these methods are reasonably stable in some environments, they suffer from the problem that they lack stability in biological environments of high salt and high protein concentration. The PAA-PEG complexes therefore quickly destabilise and eventually disintegrate, thereby releasing the biomolecule payload molecule in areas remote from the intended target site. Accordingly, they have limited application in environments of high salt and/or protein concentrations. In order to prevent this disintegration from occurring, PAA complexes can be stabilised using physical cross-links between neighbouring PAA chains. In addition, for marine environments, where high salt concentrations exist, and polluted environments where high concentrations of various chemical agents are present, stabilisation of PAA complexes by physical cross-linking would also be highly desirable.

Due to their hydrophilic nature, when cross-linked, PAAs can form hydrogels. PAA hydrogels have the potential to act as scaffold structures in tissue engineering applications. Furthermore, PAA-based hydrogels have also been shown to act as biodegradable and biocompatible substrates for cell culturing techniques.

Cross-linked PAAs may be obtained by various methods. For instance, PAAs bearing vinyl bonds that are regularly distributed along the main chain, obtained by co-polymerisation with suitable monomers, such as allylamine, can be employed for cross-linked resins by radical post-polymerisation. Another procedure is to employ multi-functional amines as cross-linking agents between neighbouring PAA chains. For instance, diaminoalkanes contain four mobile hydrogens and behave as tetrafunctional monomers, which favour inter-chain connections or cross-links between neighbouring PAA chains.

There is therefore a significant need for the preparation of reducible (i.e. reversible) cross-linked PAA complexes, which can be used in various medical and environmental applications, for example, for delivery of biological payload molecules. A number of research groups have devised strategies in which polyelectrolyte complexes with cationic polymers such as polyethylenimine (PEI) and poly-L Lysine (PLL) can be stabilised by cross-linking. An early procedure used cleavable cross-linkers to stabilise the surface of pre-formed polyelectrolyte complexes. Another strategy involves template oligomerisation in which very small polycations are used, which are then polymerised, and/or cross-linked in the presence of DNA. In a modification of this strategy, a larger oligomer is either cross-linked or linked using disulphide bonds to give a linear chain of small polyion segments which are assembled separately, or with the DNA to give a reducible, high molecular weight polymer. Non-reducible linkages may be used, but are less active in terms of DNA transfection activity.

There are several reasons for the use of these various strategies to cross-link polyelectrolytes. In general, smaller polycations do not condense DNA efficiently or stably. However, the toxicity of cationic polymers is usually dependent on molecular weight, and so the use of high molecular weight cationic polymers increases the toxicity of the complex, and therefore limits its application particularly in the medical field. There is thus a balance which in these cases can be solved by producing cleavable higher molecular weight polymers which also provide an improved release mechanism for the payload DNA molecule.

In the case of PAAs which have a lower intrinsic toxicity, a different strategy is possible. In this case larger polymers may be used, which are simply cross-linked for stability and cleavable to release the DNA. The inventors of the present invention have previously disclosed a procedure for producing sterically-stabilised PAA complexes based on PEG-PAA-PEG triblock copolymers (Biochimica et Biophysica Acta 2002, 1576, 269-286). However, the inventors have found that in the case of PAAs, it is not possible to easily form cross-links to produce a reducible, and therefore, reversible cross-linked PEGylated PAA structure. This is because there is no free amine group available in the structure to form cross-links after the assembly of the PAA chain.

It is therefore an object of the present invention to obviate or mitigate one or more of the problems of the prior art, whether identified herein or elsewhere, and to provide a simple, inexpensive and convenient synthetic route for the assembly of sterically stabilised, reducible (i.e. reversible) cross-linked, PAA complexes, which are also non-toxic. It is also an object of the invention to provide various applications, biological or otherwise, for the use of sterically stabilised, reducible cross-linked, PAA-PEG copolymers, and delivery systems produced with these polymers.

The inventors of the present invention investigated ways in which a reducible cross-linked PAA complex could be produced using chemical synthetic routes. They believed that one suitable mechanism for cross-linking neighbouring polymer chains could be to incorporate sulphur atoms into each PAA molecule so that disulphide bonds (i.e. cross-links) could be formed therebetween.

Accordingly, the inventors attempted to react pyridyldithioethylamine (prepared by a first step of reacting aldrithiol-2 with aminoethane thiol) with a polyamidoamine. However, a problem with this system is that the majority of the product decomposes under the conditions of PAA polyaddition. Furthermore, this reaction scheme also involves several steps. In order to solve these problems, the inventors considered an alternative synthetic route.

The inventors devised a new reaction scheme, one embodiment of which is shown in Scheme 1. Firstly, a bisacryloyl compound is reacted with a primary amine and/or a secondary di-amine, one or both of which contains a disulphide group, to form a first intermediate compound comprising a polyamidoamine polymer having pendant groups containing disulphide moieties. This first intermediate is then reduced so that the disulphide moiety is cleaved to form a second intermediate compound comprising a polyamidoamine polymer having pendant groups containing sulphydryl groups (or thiol groups). The second intermediate compound may be oxidised (for example in air) so that intermolecular disulphide bonds are formed between the pendant sulphydryl groups, thereby forming cross-links and yielding a cross-linked PAA composition comprising cross-linked polyamidoamine (PAA), in which cross-links are formed between the corresponding pendant sulphydryl moieties. The cross-linked composition was a gel or hydrogel in nature.

As shown in Scheme 1 the first step of the reaction may also involve the reaction with amine molecules that do not contain disulphide groups, for example, on either the primary amine or the secondary di-amine. By appropriate choice of the reactants and their proportions, control may then be exercised over the level (i.e. concentration, position and spacing) of pendant disulphide moieties that are incorporated into the final composition that is prepared. Such amine molecules that do not contain disulphide groups are most conveniently secondary amines.

Furthermore, as also indicated in Scheme 1, the free SH groups of the second intermediate compound may be activated to facilitate cross-linking. As illustrated, such activation may be by reaction with a suitable activation agent, such as bipyridyl disulphide. As illustrated in the Examples, and in particular Example 11, the reaction was surprisingly successful and converted the substantially liquid reactants (i.e. non-cross-linked composition) into a substantially gel-like product (i.e. cross-linked composition). Hence, the inventors have successfully demonstrated a novel reaction scheme for preparing sulphydryl-containing PAA polymers, in which the sulphydryl groups react to form cross-links, and thereby form a hydrogel. The inventors believe that, to date, cross-linked complexes of PAA have not been reported. Furthermore, the inventors went on to demonstrate that by adding a suitable reducing agent to the cross-linked hydrogel composition, or placing the hydrogel under certain conditions such that reduction can occur, it is possible to reverse the cross-linking reaction to thereby produce a solution of PAA polymer having non-cross-linked pendant sulphydryl groups. The inventors believe that they are the first to prepare such a reducible, cross-linked PAA polymer composition.

Therefore, according to a first aspect of the present invention, there is provided a composition comprising a polyamidoamine (PAA) polymer comprising a pendant disulphide, sulphydryl, or activated sulphydryl moiety.

By the term "pendant moiety", we mean a group that is attached to the main chain of the PAA polymer, but which is not part of the main chain.

Preferably, the composition comprises a linear polyamidoamine (PAA) polymer comprising a pendant disulphide, sulphydryl, or activated sulphydryl moiety.

By the term "linear PAA polymer", we mean a single chain of monomers with no branch points, thus excluding dendrimers or other branched structures.

Preferably, the composition according to the first aspect is adapted to form cross-links between the pendant disulphide, sulphydryl, or activated sulphydryl moiety. In the invention, such cross-links involve the formation of disulphide bonds.

When the composition does not comprise cross-linked PAA polymer chains, it may have the form of a solution. However, when the composition is cross-linked, it forms a gel, and may be referred to as a hydrogel. Accordingly, the composition according to the first aspect may also be referred to as a "hydrogel precursor composition". Preferably, the cross-linked composition is a gel under conditions of standard temperature and pressure (i.e. 1 atm, 20° C.).

Preferably, the cross-linked composition is reducible such that upon reduction of the cross-linked composition, the cross-links between polymer chains are broken. Reduction of the cross-linked composition may be achieved by a suitable reducing agent, such as 1,4-dithiothreitol, sodium metabisulphide, or reduced glutathione. It is also noted that suitable reducing agents are also found in biological tissues, the principal agents being glutathione and cysteine.

Advantageously, the composition according to the invention is substantially non-toxic, or at least lower toxicity than known commonly used cationic polymers. In vitro toxicity values for several normal (i.e. non-amphoteric) PAAs are in the order of 0.5-4mg/ml (E. Ranucci et al., J Biomat. Sci Polymer Edn 2, 303-315,1991; ICR Hill et al., BBA 1427, 161-174, 1999). Amphoteric PAAs are usually even less toxic, with some of them being approximately as biocompatible as dextran. Therefore, it is believed that such reducible, cross-linked PAA polymers have numerous applications in medical and non-medical fields because it is possible to change the composition from solution to gel (i.e. hydrogel) states, and vice versa. Furthermore, the composition according to the invention may be used to deliver a payload molecule, for example, a biologically active payload biomolecule to a target site, as will be described hereinafter, which also has numerous biological and non-biological applications.

The PAA polymer may be synthesised from a wide range of amides and amines provided that the amine is a primary amine-terminated disulphide and/or a secondary di-amine containing a disulphide group. This is useful in varying the interaction of the resultant PAA polymer with various payload molecules. It is preferred that the PAA polymer is substantially water-soluble.

The PAA polymer according to the first aspect of the invention may contain repeating groups X and Y represented by the general formula I:—

$$\{-[X]-[Y]-\}_n \qquad \text{(Formula I)}$$

in which, n is between 5 and 500;

the groups X, which may be the same or different, are amide-containing groups of the formula

wherein $L^1$ and $L^3$ independently represent optionally substituted ethylene groups;

$L^2$ represents an optionally substituted alkylene chain; and $R^1$ and $R^2$ independently represent hydrogen or an optionally substituted alkyl group;

and the groups Y, which may be the same or different, represent amine-derived groups of the formula:—

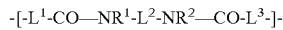

wherein $R^3$, $R^4$ and $R^5$ represent optionally substituted alkyl groups, and $L^4$ represents an optionally substituted alkylene group;

or $R^4$, $R^5$ and $L^4$, together with the nitrogen atoms to which they are attached, form an optionally substituted ring, with the proviso that at least some of $R^3$, $R^4$ and $R^5$ contain disulphide, sulphydryl or activated sulphydryl groups.

It is preferred that $R^1$ and $R^2$ are hydrogen. Where $R^1$ and/or $R^2$ represents an optionally substituted alkyl group, it is most preferably an alkyl group containing a $C_1$-$C_{20}$ chain, more suitably, a $C_1$-$C_{10}$ chain, and even more suitably, a $C_1$-$C_5$ chain.

$R^3$, $R^4$ and $R^5$ most preferably represent optionally substituted alkyl groups containing a $C_1$-$C_{20}$ chain, more suitably, a $C_1$-$C_{10}$ chain, and even more suitably, a $C_1$-$C_5$ chain.

$L^2$ and $L^4$ most preferably represent optionally substituted alkylene chains containing 1-10 carbon atoms, more suitably 1-5 carbon atoms, and most suitably 1-3 carbon atoms. $L^2$ and $L^4$ are preferably unsubstituted. $L^2$ most preferably represents —$CH_2$—. $L^4$ most preferably represents —$CH_2CH_2$—.

Where any of $L^1$, $L^2$, $L^3$ and $L^4$ are substituted, the substituents may be selected from a wide range, including without limitation alkyl, alkoxy, acyl, acylamino, carboxy, cyano, halo, hydroxy, nitro, trifluoromethyl and amino.

Where $R^1$ and/or $R^2$ is substituted, the substituents may be selected from a wide range, including without limitation alkyl, alkoxy, acyl, acylamino, carboxy, cyano, halo, hydroxy, nitro, trifluoromethyl and amino.

Where any of $R^3$, $R^4$ and $R^5$ are substituted, the substituents may be selected from a wide range, including without limitation alkyl, alkoxy, acyl, acylamino, carboxy, cyano, halo, hydroxy, nitro, trifluoromethyl and amino. At least some of $R^3$, $R^4$ and $R^5$ are substituted by groups selected from sulphydryl, activated sulphydryl and —S—S—$R^6$, wherein $R^6$ represents alkyl optionally substituted by one or more substituents selected from a wide range, including without limitation alkyl, alkoxy, acyl, acylamino, carboxy, cyano, halo, hydroxy, nitro, trifluoromethyl and amino.

Unless the context indicates otherwise, references herein to alkyl groups should 20 be taken to indicate optionally substituted alkyl groups containing a $C_1$-$C_{20}$ chain, more suitably, a $C_1$-$C_{10}$ chain, and even more suitably, a $C_1$-$C_5$ chain.

In Formula I, n may be between 5 and 400, more suitably, between 10 and 300, and most suitably between 20 and 100.

Preferably, the Molecular Weight of the PAA polymer is between 1500 Da and 120,000 Da, more preferably, between 3,000 Da and 90,000 Da, even more preferably, between 4,000 Da and 60,000 Da, and most preferably, between 6,000 Da and 30,000 Da. The inventors have appreciated the significance of their novel reaction scheme as shown in Scheme 1 used for the preparation of the composition according to the first aspect.

Accordingly, in a second aspect of the invention, there is provided a method of preparing a polyamidoamine (PAA) polymer comprising a pendant disulphide, sulphydryl, or activated sulphydryl moiety, the method comprising reacting a bisacryloyl compound with a primary amine and/or a secondary di-amine one or both of which contains a disulphide group.

One embodiment of the method of the second aspect is summarised in Scheme 1, and comprises the use of different monomers to form a co-polymer. It will be appreciated that the composition according to the first aspect, which is prepared by the method of the second aspect comprises a PAA polymer or co-polymers. Co-polymers are prepared by linking two or more linear sequences of different homopolymers together, and in cases where the homopolymers are long, a block copolymer is produced. The skilled technician will appreciate how to prepare di-block, tri-block, sandwich-block, or stereo-block co-polymers, and how to choose combinations of various monomers or co-monomers to achieve the desired polymer.

As shown in Scheme 1, and as described in the Examples, PAAs (which are preferably linear) containing a pendant disulphide, or sulphydryl, or activated sulphydryl group may be synthesised in a number of different polymer structures and sequences depending on the monomers chosen.

The bisacryloyl compound used in the method may have the formula II:—

$$CH_2=CH-CO-NR^1-L^2-NR^2-CO-CH=CH_2 \qquad \text{(Formula 11)}$$

wherein $R^1$, $R^2$, and $L^2$ are as defined in relation to Formula I.

Preferably, $R^1$ and $R^2$ are hydrogen. Preferably, $L^2$ is a $CH_2$ group. It is most preferred that the bisacryloyl compound is methylene bisacrylamide (MBA).

In preferred embodiments of the method in which a primary amine containing a disulphide is used, the primary amine containing a disulphide group may have the formula III:—

$$NH_2—R^3 \quad \text{(Formula III)}$$

wherein $R^3$ is as defined in Formula I.

Preferably, $R^3$ represents an alkyl group, most preferably $C_{1-2}$ alkyl, substituted by —S—S—$R^6$, wherein $R^6$ is as defined above and is most preferably a $C_{1-2}$ alkyl group, which may optionally be substituted.

Preferably, the primary amine containing a disulphide group is cystamine, which may be unprotected. However, preferably, a mono-protected derivative of the primary amine is used in the method. Thus, most preferably, the primary amine is cystamine, one amine group of which carries a protecting group. The inventors believe that the use of a primary amine terminated disulphide in the preparation of the composition is advantageous because it requires the use of a small number of steps, and because the majority of the product does not decompose under the conditions of PAA polyaddition. Examples 1 to 3 illustrate the method of the second aspect.

In embodiments of the method in which a secondary di-amine containing a disulphide is used, the secondary di-amine may have formula IV:

$$H—NR^4-L^4-NR^5—H \quad \text{(Formula IV)}$$

wherein $R^4$, $R^5$ and $L^4$ are as defined in relation to Formula I.

$R^4$ or $R^5$ may represent an alkyl group, most preferably $C_{1-2}$ alkyl, substituted by —S—S—$R^6$, wherein $R^6$ is as defined above, and is most preferably a $C_{1-2}$ alkyl group, which may optionally be substituted.

In one embodiment, the method according to the second aspect may comprise reacting a bisacryloyl compound with a primary amine containing a disulphide group (i.e. Formula III). In another embodiment, the method may comprise reacting a bisacryloyl compound with a secondary di-amine containing a disulphide group (i.e. Formula IV). It will be appreciated that the method may also comprise reacting a bisacryloyl compound with a primary amine containing a disulphide group, shown as Formula III, and in addition, a secondary di-amine containing a disulphide group, shown as Formula IV.

However, in order to control the level of disulphide or sulphydryl groups introduced into the PAA polymer produced, it is especially preferred that the method according to the second aspect involves the use of amine molecules that do not contain any disulphide groups. For example, the primary amine (which contains disulphide groups) may be used in conjunction with a secondary di-amine (which contains no disulphide groups) or vice versa to give a polymer with a controlled level of pendant disulphide moieties.

In a most preferred embodiment, the secondary di-amine may not contain a disulphide. Hence, referring to Formula IV, preferably, $R^4$ is methyl. Preferably, $R^5$ is methyl. Preferably, $L^4$ comprises a $CH_2$, and more preferably, $CH_2CH_2$. Hence, the secondary di-amine may preferably have formula V:—

$$CH_3—NH—CH_2—CH_2—NH—CH_3 \quad \text{(Formula V)}$$

Hence, it is preferred that a secondary di-amine is either dimethylethylenediamine (DMEDA), as shown in Schemes 1 and 4, or 2-methyl-piperazine, as shown in schemes 2 and 3.

Hence, preferably, the method according to the second aspect comprises reacting a bisacryloyl compound, preferably of Formula II, with a primary amine containing a disulphide group, preferably of Formula III, with a secondary di-amine, preferably of Formula V.

Therefore, as shown in Scheme 1, in step one of the method, the bisacryloyl compound, the primary amine containing a disulphide group and, preferably, the secondary diamine are reacted together. Suitable reaction conditions for step one comprise dissolving a bisacrylamide and BOC-cystamine in water and stirring together under nitrogen for 6 h. The diamine component is then added and reacted for a further 72 hours. The bisacrylamide is used in equimolar quantity to the sum of the diamine and BOC cystamine components. The amount of BOC cystamine can be adjusted to vary the proportion of repeating units containing a sulphydryl group. Examples 1-3 and Scheme 5 illustrate this reaction.

As shown in Scheme 1, in step two of the method according to the second aspect, the pendant disulphide may be subsequently reduced to give a free sulphydryl group. Reduction may be carried our using any suitable reducing agent known to the skilled technician, for example, dithiothreitol (DTT). Suitable reaction conditions for step two comprise a reaction in water containing tris buffer at pH 8.5 for 6 hours. For DTT, a 3-fold molar excess can be used, but for sodium bisulphite, a 1000-fold greater amount is required. Examples of polymer reduction are shown in Examples 4-9 using either sodium metabisulphite (see Examples 5, 7, and 9) or DTT (see Examples 4, 6, and 8) and the reaction shown in Scheme 6. As shown in Scheme 1, in step three of the method according to the second aspect, the free sulphydryl group may be activated upon addition of a suitable activation agent, for example bi-pyridyl disulphide, as illustrated in Examples 10 and 12, and Scheme 7. Preferably, the free sulphydryl group is reacted with a dipyridyl disulphide to give a protected/activated sulphydryl group. Suitable reaction conditions for step three comprise treating the reduced polymer with an equimolar amount of dipyridyl disulphide for 15 hours in water containing Tris buffer at pH 8.5 as detailed in Examples 10 and 12. Alternatively, as described in Example 34, 5,5-dithiobis(2-nitrobenzoic acid) may be used instead of dipyridyl disulphide as an activation agent.

As mentioned above, the composition according to the first aspect may exist as a solution under conditions in which there are few or substantially no cross-links between the PAA polymer chains. However, the inventors have found that the composition comprising linear PAA comprising a pendant disulphide, sulphydryl, or activated sulphydryl moiety provides a surprisingly useful cross-linking system, which may be modified for use in a variety of biological and non-biological applications. In particular, the inventors believe that the composition according to the first aspect may be effectively used in a method for the preparation of cross-linked compositions, such as hydrogels, which have various applications in medicine.

Therefore, according to a third aspect of the invention, there is provided a hydrogel comprising a plurality of polyamidoamine (PAA) polymer chains that are cross-linked via linking groups containing reducible disulphide bonds.

By the term "hydrogel", we mean a gel in which water is the major dispersion medium. Hence, preferably, components or subunits of the hydrogel, i.e. the cross-linked PAA polymer chains, are dispersed within water. Preferably, the hydrogel comprises at least 80% (w/w) water, more preferably, at least 90% (w/w) water, and more preferably, at least 95% (w/w), even more preferably, at least 98% (w/w) water.

The cross-linked components of the hydrogel (i.e. the PAA chains) may have a degree of polymerisation between 5 and 500, more preferably between 10 and 250 and most preferably between 10 and 100. Assuming a repeating unit molecular weight of 300, these may have molecular weight ranges of 1500 Da to 150,000 Da, and more preferably, between 3000 Da and 75,000 Da, and most preferably, between 3000 Da and 30,000 Da.

By the term "cross-link", we mean a covalent bond formed between pendant groups attached to two separate polymer chains. In the invention, such cross-links involve the formation of disulphide bonds.

Preferably, the cross-linked hydrogel of the third aspect is reducible, wherein the cross-links between PAA polymer chains may be broken when the hydrogel is reduced. Hydrogels per se are known. However, a hydrogel comprising reducible, cross-linked PAA polymers is not known, and it is this reducibility which provides significant advantages over known hydrogels.

The cross-linked PAA hydrogel (substantially insoluble) may be reduced upon contacting with a reducing agent, for example, dithiothreitol (DTT), sodium metabisulphite, or glutathione. Suitable reaction conditions for hydrogel reduction are that the hydrated hydrogel is adjusted to pH 8.5 with sodium hydroxide and reacted with either a 3 fold excess of dithiothreitol or a 3000 fold molar excess of sodium metabisulphite. This reduction reaction is exemplified in Scheme 9 and Examples 23, 25 and 27, which describe reduction with DTT and Examples 24, 26 and 28, which describe hydrogel reduction with sodium metabisulphite. This results in a corresponding (substantially soluble) composition according to the first aspect in which PAA chains have pendant groups containing sulphydryl groups.

The soluble reduced PAA composition may be purified by methods known in the art, provided that a substantially oxygen-free atmosphere is maintained. In most cases, purification is achieved by ultrafiltration (Biomacromolecules 2, 1023-1028, 2001; Biomacromolecules 6, 2229-2235, 2005; Biomacromolecules 7, 1215-1222, 2006), and as described in various examples. Hence, advantageously, the composition according to the first aspect comprising PAA polymer containing composition may be stored under inert conditions, for example nitrogen, either in the solid hydrogel state (i.e. the hydrogel according to the third aspect), or as a substantially aqueous solution (i.e. the composition of the first aspect).

If purified from the reducing agent, i.e. upon re-oxidation, then the sulphydryl bearing PAA is converted again back to the cross-linked network of the hydrogel of the third aspect. The inventors have found that air is a sufficiently strong oxidising agent, and this is shown in Examples 29, 31 and 33. Furthermore, temperature is also a factor in whether the composition is aqueous or a hydrogel. Hence, in Summer (i.e. temperatures above 30° C.), the aqueous solution may be left in a beaker for a while, and gelation will be observed as the cross links develop between adjacent PAA chains. Dilute hydrogen peroxide may also be used to cause gelation. Typically reduced polymer in tris buffer pH 8.5 would be reacted with an equimolar amount of 5% hydrogen peroxide solution for 3 hours. However, an excess (more than 1.3 times the stoichiometric amount) should be avoided.

It should be appreciated that the soluble PAA composition comprising reduced PAA (due to the action of the reducing agent) may be used to form a hydrogel directly. It should also be appreciated that activated PAA may also be used to form a hydrogel directly.

Furthermore, in a further aspect, there is provided a method of preparing a hydrogel comprising a plurality of polyamidoamine (PAA) polymer chains that are cross-linked via linking groups containing reducible disulphide bonds, the method comprising:—(i) reacting a bisacryloyl compound with a primary amine and/or a secondary di-amine one or both of which contains a disulphide group, to form PAA polymer chains, and (ii) allowing reducible disulphide bonds to form between the PAA polymer chains.

The hydrogel may be prepared in situ, for example, using unprotected cystamine as the primary amine. This method is described in Examples 20 to 22.

The inventors have found that the composition according to the first aspect, or the hydrogel according to the third aspect may be readily converted into, or synthesised as, a co-polymer with PEG, to form PEGylated cross-linkable PAAs. Inclusion of PEG into hydrogels may have a number of beneficial effects comprising improving the biocompatibility and further reducing the toxicity of the cationic polymers, and conferring long circulating properties of the hydrogels if formulated as nanoparticles. Therefore, in a preferred embodiment, the composition of the first aspect, or the hydrogel of the third aspect comprises a copolymer of polyamidoamine (PAA) comprising a pendant disulphide, sulphydryl, or activated sulphydryl moiety and PEG.

The skilled technician will appreciate the structure and behaviour of PEG, which is illustrated in Scheme 2. Preferably, the composition comprises poly(amidoamine)-(ethyleneglycol) block co-polymer. Preferably, the composition of the first aspect or the hydrogel of the third aspect comprises a block co-polymer having the structure with repeating poly(ethyleneglycol) and poly(amidoamine) blocks, wherein PEG contains between 2 and 500, and more preferably, between 10 and 250 ethylene glycol units. The inventors believe that a method for incorporating PEG into the composition of the first aspect or hydrogel of the third aspect is particularly useful.

Therefore, according to a fourth aspect of the invention, there is provided a method for preparing a composition comprising a copolymer of polyethylene glycol (PEG) and polyamidoamine (PAA) comprising a pendant disulphide, sulphydryl, or activated sulphydryl moiety, which may or may not be cross-linked, the method comprising contacting monomers of polyamidoamine (PAA) comprising a pendant disulphide, sulphydryl, or activated sulphydryl moiety with amine-terminated PEG; and allowing the corresponding copolymer to form.

The inventors have devised a novel method according to the fourth aspect for preparing PEGylated cross-linkable PAA's. Steps (a) to (e) of Scheme 2 illustrate an embodiment of the method of the fourth aspect resulting in the preparation of a PEGylated PAA co-polymer, where n refers to the number of PEG monomers. Hence, PEG may be reacted with a suitable polymerisation activator, such as, carbodiimide (CDI) to produce a PEGylated structure. Suitably, n (shown in Scheme 2) may be between 0 and 100, more suitably between 5 and 80, and more suitably, between 10 and 50. The product of this step (c) may be mixed with a primary amine terminated disuiphide (b) and/or a primary amine or secondary di-amine (a) in a ratio of a+b+c=1, and reacted with a bisacrylamide as in the method of the second aspect. Preferably, the total amount of the reactants a+b+c is substantially equal to the amount of bisacrylamide.

As shown in Scheme 2, the product of this step is a linear PAA multi-block copolymer comprising a polyamidoamine polymer having pendant groups containing disulphide moieties. This may be reduced with a suitable reducing agent so that the disulphide moiety is cleaved, and replaced by hydrogen to form a second intermediate compound comprising a polyamidoamine polymer having pendant groups containing sulphydryl groups (i.e. a thiol group). The second intermediate compound may be oxidised (for example, in air) so that intramolecular disulphide bonds are formed between the pendant sulphydryl groups thereby forming cross-links and yielding a cross-linked PAA composition comprising cross-linked polyamidoamine (PAA), in which cross-links are formed between the corresponding pendant sulphydryl moieties. The cross-linked composition is a hydrogel at STP. Alternatively, the second intermediate compound may be reacted with a suitable activating agent, such as, pyridyl disulphide to produce a polyamidoamine (PAA) comprising a pendant sulphydryl moiety, which in turn forms the composition comprising cross-linked polyamidoamine (PAA) comprising a pendant sulphydryl moiety. The resultant product is a multi-block linear PEG-PAA copolymer containing a pendant sulphydryl group for cross-linking.

Alternatively, a PEG-PAA-PEG triblock co-polymer may be produced by using a two step reaction in which a small excess of bisacryloyl is present in the polymerisation reaction mixture to yield an acrylate terminated polymer. This product may then be further reacted by addition of amine-terminated PEG to give an amine terminated tri-block copolymer.

As illustrated in Scheme 3, which is another embodiment of the method of the fourth aspect, the inventors have also found that a monomethoxy (i.e. mono-protected) PEG may be modified with a primary di-amine, which may be subsequently reacted with other co-monomers to give a comb PEG-PAA copolymer with the PEG chains pendant to the main polymer chain. By the term "comb copolymer", we mean one where the polymer chains (e.g. PEG) are fixed to (i.e. pendant to) the main polymer chain (e.g. PAA) in the manner of teeth on a comb.

In this embodiment of the method, the sequential addition of diamine modified monomethoxy PEG after PAA synthesis advantageously results in a PEG-PAA-PEG tri-block conformation with methoxy protected end groups, as shown in Scheme 4.

The inventors believe that the composition and hydrogel according to the invention will have considerable utility in many biomedical settings, for example, in the delivery of payload biomolecules to a target site.

Hence, according to a fifth aspect of the invention, there is provided a delivery composition for delivering a payload molecule, the delivery composition comprising a payload molecule combined with the composition according to the first aspect, or a hydrogel according to the third aspect.

According to a sixth aspect of the invention, there is provided a method for preparing the delivery composition according to the fifth aspect, the method comprising contacting a payload molecule with the composition according to the first aspect, or a hydrogel according to the third aspect, and exposing the mixture to conditions such that the payload molecule combines with the composition or hydrogel, thereby forming a payload delivery composition according to the fifth aspect.

The delivery composition may be a solution or a hydrogel, and may take on any form or dimension depending on the payload molecule to be delivered, and the specific application required. For example, if the payload molecule is polyanionic molecule, such as DNA, then upon complexing with a cationic polymer such as PAA, there is a mutual neutralisation of charges. This neutralisation leads to a loss of hydrophilicity, and the resulting loss of water molecules from the complex drives the condensation of particles into a tightly wound structure. In such cases, a hydrogel would not be formed. Accordingly, preferably, the payload delivery composition may comprise a carrier particle, for example a microparticle or a nanoparticle.

Hence, in a seventh aspect, there is provided a carrier particle adapted in use to carry a payload molecule to a target site, the carrier particle comprising the composition according to the fifth aspect, wherein the payload molecule is capable of being active when the particle is at least adjacent the target site.

The payload molecule may comprise a biologically active compound (or biomolecule). By the term "biomolecule", we mean any organic molecule with a biological activity and/or specificity, i.e. the compound has a biological effect on reaching the target site. The biomolecule may be a macromolecule from a living organism. For example, the payload molecule may comprise a whole cell, or part of a cell, a virus, phage, or a micro-organism, or an organelle, or a virus particle etc, an amino acid, peptide, protein, enzyme, antibody, or a polysaccharide. The payload may alternatively comprise other molecules or constructs such as dye or particulate materials such as microparticles, nanoparticles or other polyelectrolyte complexes.

However, preferably, the payload molecule comprises a biologically active polyanionic molecule, which preferably, comprises a regular array of negative charges therealong. For example, the payload molecule may comprise a nucleic acid or a derivative thereof. The payload molecule may comprise DNA or cDNA or RNA (e.g. mRNA, siRNA, or tRNA). Advantageously, electrostatic attraction occurs between the positive charges of the PAA polymer and negative changes of the polyanionic molecule, e.g. the phosphate backbone of DNA, to form a polyelectrolyte complex which improves the capability of the carrier particle to bind with, and thereby carry, the payload.

The target site may be a target biological environment requiring the delivery of the payload molecule, for example, a treatment site of a patient, for example, a wound site. The target site may be a body fluid, an organ, tissue, a cell, or group of cells, such as a tumoral mass. Depending on the application, the target site may be intracellular (e.g. for DNA delivery) or extracellular (e.g. hydrogel matrix). Accordingly, the target site may be outside a cell, i.e. the extracellular matrix, or the cell surface.

Suitable sizes of the carrier particle may vary according to the payload and usage. For some usages, e.g. DNA delivery, a nanoparticle sized formulation may be preferred in which case the carrier particle may be in the size range 10 nm to 500 nm, or more preferably, 20 nm to 250 nm, or most preferably between 30 nm and 100 nm. As illustrated in FIGS. 13, 14, 16 and 17, particle sizes may be between 30 nm to 170 nm.

For other usages, eg incorporation of a low release protein, a micrometre sized carrier particle may be preferred with a size range of 0.5 to 20 micrometres or more preferably 1 micrometre to 5 micrometres. Preferably, the carrier particle is substantially spherical in shape, and hence, the dimensions given above are the average diameter of the particle. However, depending on the environmental conditions, an original particle having spherical geometry may be modified to an elliptical shape.

Due to the considerable physical barriers presented to payload molecules for their delivery to cells and tissues, it may be preferred to incorporate various additional moieties into the compositions or hydrogel according to the invention, and in particular, the PAA polymer thereof. By way of example, the PAA polymer may additionally comprise cell surface targeting ligands, or cell binding ligands, or nuclear targeting sequences etc, which facilitate delivery of the carrier particle to the cell nucleus.

Advantageously, the chemistry of the PAAs described herein readily lends itself to the incorporation of such additional moieties and ligands within the delivery system or the carrier particle. For example, amine terminated PEG-PAA-PEG triblock copolymers may be readily produced in the modification of Scheme 2 allowing addition of biological recognition ligands, for example, for cell targeting and uptake. Incorporation of other pendant groups or moieties within the polymer is also possible, and may be useful for incorporation of other biological functions within the PAA polymer, for example incorporation of membrane penetrating peptides or nuclear localisation sequences, which are well known to the skilled technician.

The inventors investigated a method for incorporating a payload molecule, such as DNA, into the composition of the first aspect or the hydrogel of the third aspect in order to prepare the composition of the fifth aspect, which may be used to form a carrier particle of the seventh aspect. The carrier particle is shown in FIG. 12. As illustrated in Scheme 4, which is one embodiment of the method according to the sixth aspect, the inventors have found that polyion micelles containing a payload molecule, such as DNA, may be produced by mixing PEGylated cationic polymers with DNA. In one embodiment of this method, this may be achieved by producing a PEG-PAA-PEG, as described in relation to the method according to the second aspect relating to Schemes 2 or Scheme 3, and using the sulphydryl containing PAA described in Scheme 1 as a cross-linker. This short cross-linking co-polymer may be a random co-polymer with a small concentration of pendant disulphides. Alternatively, PAA polymers with terminal disulphide groups may be produced by sequential reaction polymer components, firstly using a mixture of bisacryloyl and diamine components, and then subsequent addition of the bisacroyloyl with the monoprotected cystamine.

In order to produce suitable complexes, and hence, suitable carrier particles according to the invention, the inventors have found that it is advantageous to maintain an appropriate ratio of PAA polymer to payload molecule, which, if DNA is used, is the PAA:DNA ratio. The inventors have previously shown that PEG-PAA's may produce sterically stabilised polyelectrolyte complexes with DNA by combining PAA and PEGylated PAA (PEG-PAA-PEG) in suitable proportions to give appropriate PEG to PAA ratios. Hence, in considering the optimisation of these polyelectrolyte complexes, the location of the sulphydryls in the PEG-PAA-PEG may be best placed immediately between the terminus of the PAA and the start of the terminal PEG moieties in order to allow simple reduction of the complex when required to thereby release the payload molecule. In this case, an embodiment of a scheme to yield a controlled number and location of sulphydryl moieties, which may be preferred, is illustrated in Scheme 4.

Assembly of the carrier particle may be accomplished by methods as disclosed in Rackstraw et al (Biochimica et Biophysica acta 1576, 269-286, 2002). In this paper, it was shown that a mixture of PAA and PEG-PAA-PEG mixed with DNA gave reproducible small sterically stabilised complexes, but the quality of the complexes can be affected by the order of addition of reagents. If using polymers containing free sulphydryl groups, a similar method can be used. Alternatively, if using activated sulphydryl groups on one of the components, the short PAA may be mixed with the payload molecule (e.g. DNA), followed by the PEG-PAA-PEG. The proposed structure of the surface of the carrier particle according to the seventh aspect is illustrated in FIG. 12. Although the inventors do not wish to be bound by any hypothesis, they believe that the short PAA forms a loose complex with the DNA. On addition of the PEG-PAA-PEG, the DNA becomes fully condensed with the PEG chains facing the external medium. The PAA already present, then cross-reacts with the pendant sulphydryl groups on the PAA-PEG.

Advantageously, and preferably, the carrier particle may be reduced with a suitable reducing agent. These could include either reduction in vitro with reducing agents such as DTT or mercaptoethanol to recover DNA, or reduction in situ in a cellular environment by biological reducing agents such as glutathione or cysteine. Such reduction causes the cross-links between the PAA chains to be broken, thereby causing the particle to disintegrate, thereby releasing the payload molecule (e.g. DNA) at the target site. Because the activity of the payload molecule is retained within the carrier particle, advantageously, the carrier particle is therefore an efficient delivery system.

The inventors conducted further investigations to support the use of PAA polymers according to the invention for the preparation of the carrier particle according to the seventh aspect of the invention, and in particular, nanoparticles (polyelectrolyte complexes) containing DNA which are cross-linked to improve their stability. Furthermore, the inventors investigated the method according to the sixth aspect, for preparing the delivery composition according to the fifth aspect. The PAA polymers used in these experiments involved using a combination of PEGylated PAA (as used in the method of the fourth aspect) and also a non-PEGylated polyamidoamine, and the inventors found to their surprise that this combination of PEGylated and non-PEGylated resulted in the production of particles with improved stability.

Hence, preferably, the composition according to the fifth aspect, the method according to the sixth aspect, and the carrier particle according to the seventh aspect comprise use of PEGylated and non-PEGylated polyamidoamine (PAA). Hence, preferably the PAA-based composition comprises a PEG-PAA-PEG or PEG-PAA copolymer, and a PAA homopolymer, both containing pendant sulphydryl groups. Examples 47 to 50 summarise the data, and a number of polymers with different specifications were made.

The inventors made numerous suitable copolymers, the chemistry of which are illustrated in reaction schemes 10 to 12.The inventors have named their preferred polymers as Complexing Polymers (CP). Reaction Scheme 10 illustrates the syntheses of suitable CP precursor molecules, and reaction Scheme 11 illustrates the synthesis of preferred Complexing Polymers from these precursors. FIG. 19 shows a general formula for preferred CP polymers, in which "a" and "b" may be independently between 1 to 200, preferably from 1 to 100, and more preferably between 1 and 50. Preferred CP polymers include CP03 (in which a is 16, and b is 15), CP04 (in which a is 16, and b is 48), and CP05 (in which a is 45, and b is 48).

However, a preferred PEG-PAA-PEG copolymer based composition comprises CP06 (ie Complexing Polymer 06), which is described in detail in Example 45. As shown in FIG. 19 for CP06, "a" is 16, and "b" is 15.

The inventors also made a batch of cross-linking homopolymers (XLPs) and then fractionated this batch based on molecular weights. Reaction Scheme 12 and Example 46 describe the synthesis of various preferred XLP polymers according to the invention. Preferred cross-linking homopolymers (XLPs) include XLP-30K (30 kD), XLP-5K (5 kD), XLP-3K (3 kD), and XLP-1K (1 kD). However, a most preferred PAA-based composition (ie a homopolymer without any PEG) comprises XLP10 (10 kD), which is described in detail in Example 46.

The rationale behind the assembly of these PAA polymers in particles according to the seventh aspect follows that of the Rackstraw paper supra. The guiding principal was that preferred complexes are formed by particular combinations of the three components, PEGylated PAA, non-PEGylated PAA and nucleic acid (NA), in which the PEG-PAA ratio and the overall PAA to Nucleic acid ratio is optimised.

It will be appreciated that as the specifications of the PEGylated polymer change (ie different PAA chain lengths and different polymer lengths), there could be a large possible number of different PEG-PAA-PEG: PAA:NA combinations which could generate optimum complexes, and hence, carrier particles according to the invention. The inventors have explored the optimum conditions for polymers of different specifications, and have investigated a range of PAA polymer and DNA ratio combinations in order to be sure that an optimum formulation has been obtained.

Assembly of the particles according to the invention is due to an interaction of the PAA polymer with the nucleic acid (eg DNA) irrespective of whether the PAA is contributed by the homopolymer or the copolymer. Tightly bound complexes depend on the PEG only occupying the surface of the particles, and so will be related to the PEG:total PAA ratio, but this will also depend on the surface area to volume ratio and also the molecular weight of the PEG moiety.

It will be appreciated that the size of optimised particles is largely dependant on the size of nucleic acid chain incorporated therein. For example, for carrier particles of a minimum size (ie less than 100 nm, for example about 30-40 nm diameter) and with a PEG molecular weight of 1700-2000, a preferred PEG:total PAA ratio in terms of Mn (number average molecular weight) of polymer components of between 1:9 and 1:12 has been determined. However, the inventors have found that well formed complexes may also be obtained over the range of ratios from 1:4 to 1:17.

Thus, the preferred range of Mn ratios of PEG:total PAA for these particle specifications may be from about 1:4 to 1:17, more preferably 1:7 to 1:15, but most preferably from about 1:9 to 1:12.

It should be appreciated that preferred ratios will decrease in proportion to the surface area to volume ratio of the carrier particle construct (the constructs can assume either a spherical or a toroidal geometry depending on formation conditions) and would also be expected to decrease with a decrease in the molecular weight (MW) of the PEG component.

One of the advantages of using a PEGylated PAA and PAA combination is that it is possible to form complexes which result in no excess of either nucleic acid (eg DNA) or polymer thus giving a 100% efficiency of particles with no clean-up necessary. For the MBA-DMEDA polymer shown in FIGS. 13 to 18, preferred PAA:NA ratios are the range from 0.5:1 to 2:1. It will be appreciated that for PAAs, the ratios are defined by the polymer repeat unit molecular weight compared to the molecular weight of an average nucleotide. However, a preferred PAA:NA ratio is between about 1:1 to 1.5:1.

In addition, the inventors have also explored the number and arrangement of pendant sulphydryl groups in the PAA polymers used to ensure that good cross-linking is obtained. Different degrees of stability of the particle may be required for different applications. Conversely the ability to reduce the cross-links and release the nucleic acid (eg DNA) will become more difficult as the number of reducible cross-links increases. The data presented in the examples is the first evidence of a polymer specification that will produce cross-linked particles according to the invention.

The inventors have demonstrated that a sufficient cross-linking for stability occurs with a formulation in which there are on average eight reducible sulphydryl groups per PEG-PAA-PEG polymer arranged with four groups at each end of the chain, and which would assemble at the surface of the carrier particle However, a formulation with just 4 sulphydryl groups do not appear to provide extra stability. The cross-linking polymer contained a pendant sulphydryl group in 25% of the repeating units equivalent to 1.5 cross-linking groups in the cross-linker compared to the PEG-PAA-PEG polymer.

Hence, the inventors have demonstrated that the number of pendant disulphide, sulphydryl, or activated sulphydryl moieties from the polyamidoamine (PAA) polymers (PEGylated and non-PEGylated) is an important factor in determining the characteristics of the resultant carrier particles. Preferably, the composition according to the invention comprises a minimum of six reducible sulphydryl groups per PEG-PAA-PEG chain which are required for stability, and preferably a minimum of eight reducible sulphydryl groups per PEG-PAA-PEG chain. A greater number of reducible sulphydryl groups may be required if increased carrier particle stability is required by the particular application. The cross-linking polymer preferably contains 1-2 times the amount of pendant sulphydryl group as contained in the PEG:PAA:PEG copolymer.

Hence, it is most preferred that the number of pendant disulphide, sulphydryl or activated sulphydryl moieties from the PEG-PAA component is a minimum of six, or more preferably eight, and that the amount of pendant disulphide, sulphydryl or activated sulphydryl moieties in the PAA component is between 0.5 and 2 times that of the PEG-PAA component, and most preferably between 1 and 1.5 times that of the PEG-PAA component.

Some results are also shown on variations in the method used for forming the composition according to the fifth aspect and the particles according to the seventh aspect, using the method according to the sixth aspect. The inventors varied the volumes (ie concentrations) of reagents (ie the PEGylated PAA, the non-PEGylated PAA, and the DNA) used in the preparation of the particles, and also the order in which the different reagents were added to each other during the method. There are clearly a number of ways that the three reagents may be mixed together. Hence, the method according to the sixth aspect may comprise reacting PEGylated PAA polymer with nucleic acid, followed by reaction with non-PEGylated PAA. Alternatively, the method may comprise reacting non-PEGylated PAA with nucleic acid followed by reaction with PEGylated PAA.

However, preferably the method comprises reacting PEGylated PAA with non-PEGylated PAA, followed by reaction with nucleic acid. Surprisingly, adding the nucleic acid (ie DNA) to the polymers last results in improved compositions and particles being produced.

The inventors found it difficult to devise simple ways of measuring whether cross-linking had taken place in the formation of carrier particles of the invention, and also how effective it was. Accordingly, FIGS. 16 and 17 provide some data on the stability of the particles by measuring the size of the particles in the presence of different salt concentrations using the highly disruptive salt sodium sulphate. Poorly stabilised particles would be expected to show a loosening of the complexes represented by a larger particle size. These results have been carried out for the range of different component ratios and the different assembly methods, and these results generally correlate with other methods suggesting whether any cross-linking has occurred.

While they do not wish to be bound by hypothesis, the inventor's ideas on stability relate to polyelectrolyte theory which suggests that the complexes formed are in equilibrium, although the inventors believe that this equilibrium is strongly in favour of particle formation and so the particles should be relatively stable unless in the presence of high salt concentrations, which should disrupt the complexes.

In looking at methods of determining particle stability, the inventors have found that for complexes in quite high concentrations, salt is not very disruptive of the particles, but that blood serum proteins are much more so. However, under these conditions of relatively high particle concentrations, these conditions do not disrupt complexes completely.

The methodology used for determining cross-linking arises from an experiment on purification of particles. Surprisingly, the inventors have found that when non-cross-linked particles are washed extensively on an ultrafiltration membrane (eg 100,000 DaMW cut off), they dissociate, pass through the filter and then re-associate on the other side. Based on these surprising findings, the inventors believe that it is unlikely that just using long PAA polymers without degradable cross-links would be a suitable way of stabilising these delivery systems, whether for gene delivery in high protein concentration environments in vivo, or for environmental applications where a high dilution is expected. The cross-linking method according to the invention is therefore likely to be important for both of these applications Using filtration and examination by transmissible electron microscopy (TEM) was the only successful method that the inventors have found to demonstrate unequivocally that cross-linking the nanoparticles had been achieved. Accordingly, FIG. 18 shows TEM images from the most preferred formulation using a couple of representative fields under the microscope.

It will be appreciated that the various compositions, hydrogel and carrier particle according to the invention have many applications both in the medical and non-medical fields. An example of a preferred non-medical application involves the tracking of a water source in the environment. Currently, water sources from any water supplier may be tracked using a fluorescent dye. A coloured dye is added at the source of the water, and the flow of the water may be monitored by tracking the position of the dye. However, when additional water sources need to be tracked in the same environment, a different dye is required so as the different water sources are not confused. It will be appreciated that there is only a limited number of suitable dyes that may be used in these circumstances, and so eventually, the number of available dyes that may be used to track water sources runs out when many water sources need to be tracked. The inventors believe that this problem may be solved by using the carrier particle according to the ninth aspect to track the flow of any fluid source in the environment.

Hence, in an eighth aspect of the invention, there is provided a fluid tracking system for tracking fluid flow, the system comprising a carrier particle according to the seventh aspect, and detection means for detecting the payload molecule.

Hence, preferably the payload molecule comprises a fluid tracker molecule, which may be detectable using suitable detection means.

The invention is also directed, in a ninth aspect, to a method of tracking fluid, the method comprising the steps of:
(i) applying a carrier particle according to the seventh aspect comprising a detectable payload molecule to a fluid at a first location; and
(ii) detecting the payload molecule at a second location of the fluid.

Advantageously, and preferably, the carrier particle, and hence, payload molecule, is stable in the fluid, which may be water. The tracking system may be used to track water in the environment. The carrier particles can travel long distances in the fluid and may be used to check the direction of travel of the fluid, e.g. in a sewer system.

The particle may be added to the fluid at the first location (this is referred to as the source). The payload molecule may be detected in the fluid at the second location of the fluid (this is referred to as the test position) while still in the carrier particle. However, preferably, the method comprises a step (before step (ii) of the method) of isolating the particle from the fluid at the second location prior to detection of the payload molecule with the detection means. The method preferably comprises a step of isolating the payload molecule from the carrier particle prior to detection. The isolation step may comprise reducing the carrier particle to release the payload molecule prior to detection. Reduction may be achieved by adding a reducing agent, such as 1,4 dithiothreitol, dithioerythritol, sodium metabisulphite or reduced glutathione.

The payload molecule preferably comprises a biomolecule, such as a peptide or protein. However, it is preferred that the payload molecule comprises nucleic acid, and preferably DNA, which is detectable by suitable detection means, e.g. PCR. This DNA is therefore referred to as "detection DNA". In such cases, the detection means may be a DNA sequencer or PCR machine.

The payload molecule may comprise a single stranded oligonucleotide, which is preferably synthetic. For example, the oligonucleotide may be in the range of about 40-80 nucleotides long having a pre-determined sequence. It will be appreciated that the specific sequence of the biomolecule is not key to the invention; it is the fact that the sequence acts as a marker, fingerprint or barcode, and is detectable. Hence, it is possible to change the nature of the payload molecule (e.g. the sequence of the protein or DNA), and therefore use different payload molecules and/or sequences thereof for different carrier particles, and thereby track different fluid flows in the same area simultaneously.

In addition to the detection DNA, the payload molecule may also comprise a carrier compound, which may be carrier DNA. The carrier DNA may be degraded, and may be crude salmon sperm DNA that has been cleaned up and fractionated to give a preparation of mainly single stranded DNA molecules of mixed sequence with approximately the same size as the detection DNA. The mixture of detection DNA and carrier DNA (i.e. the payload molecule) is then incorporated into the cross-linked carrier particle of the invention. Advantageously, the use of carrier DNA reduces the cost of the system. The ratio of detection DNA to carrier DNA may be in the region of 1:10 to 1:1000.

The carrier particle used in the system of the eighth aspect may comprise less than 50 copies of the detection DNA, preferably, less than 30 copies, and most preferably, less than 10 copies of the detection DNA. Surprisingly, the inventors believe that only one copy of detection DNA is required per carrier particle. The detection step may comprise use of PCR to determine that carrier DNA is present and in what quantity.

In summary, the inventors have demonstrated that a composition of the first aspect, which comprises a polyamidoamine (PAA) polymer comprising a pendant disulphide, sulphydryl, or activated sulphydryl moiety or the composition of the fifth aspect, which includes a payload molecule, may be used to prepare a hydrogel of the third aspect by automatic cross-linking. PEG may also be added to improve the properties of the hydrogel. Surprisingly, the inventors have demonstrated that the compositions according to the invention produce stable hydrogels under physiological conditions. Furthermore, they also found that the hydrogels formed by the cross-linked composition are adapted to support biomolecules, such as, cells, peptides or DNA molecules. Moreover, advantageously, the cross-linked PAA hydrogels are reducible so that a solution of non-cross-linked PAA polymer can be formed from the gel. Hence, the inventors believe that the hydrogels formed by such cross-linking PAA-containing compositions, the non-cross-linked solutions themselves, and also the carrier particle described herein may be used in a wide range of medical applications.

Therefore, according to a tenth aspect of the invention, there is provided a composition according to either the first or fifth aspect, or a hydrogel according to the third aspect, or a carrier particle according to the seventh aspect, for use as a medicament.

Examples of specific ailments, which may be treated with the medicament, include tissue engineering and regeneration scenarios.

Hence, in a further aspect, there is provided a composition according to either the first or fifth aspect, or a hydrogel according to the third aspect, or a carrier particle according to the seventh aspect, for use in the treatment of a medical condition characterised by tissue loss or damage.

Furthermore, according to an eleventh aspect of the invention, there is provided use of a composition according to either the first or fifth aspect, or a hydrogel according to the third aspect, or a carrier particle according to the seventh aspect, for the manufacture of a medicament for the treatment of a medical condition characterised by tissue loss or damage.

In addition, the compositions according to either the first or fifth aspect, or a hydrogel according to the third aspect, or a carrier particle according to the seventh aspect may be used in various methods of medical treatment, such as treating tissue loss or damage.

Therefore, according to a twelfth aspect, there is provided a method of treating, preventing or ameliorating an individual suffering from a medical condition characterised by tissue loss or damage, the method comprising administering to an individual in need of such treatment a therapeutically effective amount of a composition according to either the first or fifth aspect, or a hydrogel according to the third aspect, or a carrier particle according to the seventh aspect.

The inventors envisage that the method according to the twelfth aspect may be used for treating a wide range of medical conditions characterised by tissue loss/damage. Examples of conditions that may be treated include the treatment of wounds, and related injuries, tissue degenerative disorders and loss of tissue function. For example, the wound may be chronic, and may be abrasive, for example, burns. The wound may be formed by pressure, such as decubitus ulcers, and bed-sores. The wound may be acute, and may be penetrative such as a cut, or a stab wound, or the result of a crush to the body of the individual requiring treatment, or through drug induced damage or aging.

Specific tissue degenerative disorders that may be treated using the method include neurodegenerative, intervertebral disc disorders, cartilage or bone degeneration such as osteoarthritis, osteoporosis, liver degenerative disorders, kidney degenerative disorders, muscle atrophy, nerve damage or loss.

It will be appreciated that the composition comprising the sulphydryl containing PAA polymer either with or without a payload molecule may be used to form the hydrogel of the third aspect at the treatment site, and this enables the formation of a hydrogel scaffold structure, which is adapted to support cell growth. The inventors believe that cells will be able to infiltrate the hydrogel at the treatment site, thereby forming a cell culture or tissue therein. This tissue may then replace and/or repair the tissue lost or damaged at the treatment site. If a payload molecule is included, then this may be used to enhance or accelerate tissue regeneration.

In a first embodiment of the method according to the twelfth aspect, the hydrogel may be formed prior to administration to the individual, for example, in a mould using the method of the second or fourth aspect, if PEG is required. Once formed, the hydrogel may then be administered to the treatment site in the individual Again, this may be with or without a payload molecule.

In a second embodiment, an aqueous hydrogel precursor composition (i.e. the composition of the first aspect) may be introduced to the treatment site, which may then be induced in situ using the method of the second or fourth aspect to form the hydrogel of the third aspect. Hence, the hydrogel may be prepared in situ in the treatment site, with or without a payload molecule.

The aqueous precursor composition preferably comprises the bisacryloyl compound and a primary amine or secondary amine containing a disulphide group, which may then be exposed to conditions suitable for forming a hydrogel of the third aspect. It is preferred that the hydrogel or hydrogel precursor is provided in a physiologically acceptable excipient. By the term "physiologically acceptable excipient" we mean any suitable solution, which is capable of conferring biologically acceptable conditions on the PAA polymers such that cross-links form between polymer chains, thereby resulting in gelation to form the hydrogel. Examples of suitable excipients will be known to the skilled technician, and may comprise a physiological buffer, such as saline. Preferably, the excipient is provided at a biologically acceptable pH, which allows gelation.

The choice of whether to administer the hydrogel of the third aspect itself, or the hydrogel precursor composition of the first or fifth aspect, to the treatment site depends on the specific medical condition being treated. In either case, the subsequent hydrogel may be used as a scaffold structure to support at least one cell therein, to thereby repair the site of tissue loss or damage.

Hence, the inventors have demonstrated for the first time that PAA polymers may be prepared having a pendant disulphide, sulphydryl, or activated sulphydryl moiety, and also that these moieties readily form cross-links therebetween to form a reducible hydrogel. Hence, preferably, the excipient confers biologically acceptable conditions on the compositions such that cross-links form between the PAA polymers so that a hydrogel is formed either at the treatment site, or prior to administration thereto.

To date, the inventors believe that it has not been possible to form reducible cross-linked PAA hydrogels at biologically acceptable pH's. Therefore, the inventors believe that use of the compositions and hydrogel according to the invention is a significant advance over current technology.

Once the hydrogel has been administered to, or formed in situ in the treatment site, it may then be required to release the payload molecule, if present. Hence, preferably, the method comprises a step of reducing the hydrogel such that the cross-links are broken, thereby releasing the payload molecule into the treatment site. The reduction step may be achieved by the action of biological reducing agents present at the treatment site, for example, such as glutathione or cysteine. Alternatively, the physiologically acceptable excipient may comprise a suitable reducing agent, such that after time, the hydrogel formed in the treatment site is slowly dissolved thereby releasing the payload molecule. It is preferred that the biologically acceptable excipient is at a pH of between 5 and 9, more preferably between 6 and 8, even more preferably, between about 6.5 and about 7.5. It will be appreciated that the pH of most cells is about 7.4. Hence, a most preferred excipient has a pH of between about 7 and about 7.5. It will be appreciated that such pHs are referred to as being biologically acceptable conditions.

By the term "biologically acceptable conditions", we mean the hydrogel used in the method of the invention is substantially stable under in vivo conditions, i.e. conditions of pH, ionic strength and temperature, which would be found in vivo. The inventors envisage primarily using the method according to the second or fourth aspect of the invention, and hence, the hydrogel, to treat disorders characterised by tissue damage/loss in mammals and, in particular, man. Therefore, it is preferred that the hydrogel is formed and is stable under biologically acceptable conditions in mammals, and preferably, in man.

The inventors believe that the treatment site in the disorders being treated would be within a pH range of about 5.0 to about 9.0. However, it is preferred that the hydrogel is formed at a pH of between about 6.0 to about 8.0. As described herein, the method may be used to treat wounds. In chronic wounds, the pH may be between a 6.0 and 8.0. Hence, when treating chronic wounds, it is preferred that the hydrogel is stable between a pH of about 6.0 and 8.0, and preferably, about pH 6.5 to about 7.5.

The inventors believe that the treatment site of the individual being treated would be at a high ionic strength, i.e. about 0.1 5M. Hence, it is preferred that the hydrogel is formed at an ionic strength of between about 0.01M to about 1M, preferably, between about 0.05M to about 0.5M, more preferably, between about 0.1 to about 0.2, and even more preferably, between about 0.12M and about 0.17M.

It will be appreciated that the inventors envisage primarily using the compositions and hydrogel according to the invention to treat mammals, and in particular man. The inventors have found that it is therefore possible to induce transition of the compositions according to the invention from the solution containing non-cross-linked PAA polymer to form the cross-linked hydrogel on demand when in situ in the treatment site. Hence, preferably, the hydrogel used in the method is formed below about 40° C., more preferably below about 39° C., and even more preferably, below about 38° C. Therefore, preferably, the hydrogel is formed at a temperature of between about 36° C. to about 38° C., and most preferably, at about 37° C.

However, it should be appreciated that in chronic wounds, and also in surface organs (such as the skin, the eye etc.), the temperature may be a few degrees lower, for example, about 32° C. to 34° C. Hence, in embodiments of the method where the composition is used to treat chronic wounds or surface organs, it is preferred that the hydrogel forms at a temperature of between about 32° C. to 34° C.

Advantageously, by choosing specific monomer and co-monomers, which make up the PAA polymer, it is possible to vary the structural and functional properties of the hydrogel formed, and how it interacts and ultimately releases the payload molecule, if present. Therefore, the cross-linkable PAA polymer, and hence, the hydrogel may be specifically 'tailored', depending on the final use of the hydrogel.

It is preferred that the composition according to either the first or fifth aspect, or a hydrogel according to the third aspect is adapted to support at least one cell, to thereby form a physiologically stable cell-supporting medium or cell scaffold. Hence, the hydrogel or the composition may therefore be seeded with at least one cell.

Therefore, according to a thirteenth aspect of the present invention, there is provided a cell-supporting medium comprising the composition according to either the first or fifth aspect, or a hydrogel according to the third aspect, and at least one cell.

The cell-supporting medium of the thirteenth aspect may be referred to as a "cell-hydrogel scaffold". Preferably, the cell-supporting medium is adapted to support a plurality of cells. Preferably, the or each cell is biochemically functional in vivo. Accordingly, the plurality of cells may form a cell culture or a tissue. Because the hydrogel precursor composition of the first aspect is a solution, at least one cell may be suspended therein.

In a fourteenth aspect, there is provided a method of preparing a cell-supporting medium according to the thirteenth aspect, the method comprising the steps of:—
(i) contacting the composition according to either the first or fifth aspect, or a hydrogel according to the third aspect, with at least one cell; and
(ii) exposing the hydrogel or composition to conditions such that the at least one cell is supported thereon or therein, thereby forming a cell-supporting medium.

The method according to the fourteenth aspect may be carried out in situ in the treatment site, or remote from the treatment site, and then transferred thereto. The skilled technician will appreciate how to culture various cell types with the hydrogel or compositions according to the invention. Hence, it will be appreciated that the specific details of the methodologies (culture time, temperatures, growth media etc) used will depend on the type of cell involved, and the final use of the cell-supporting medium (ie. the cell-hydrogel scaffold).

However, step (i) of the method according to the fourteenth aspect may comprise contacting the solution of hydrogel precursor composition according to the first aspect or the delivery composition of the fifth aspect with the at least one cell. In another embodiment, step (i) of the method may comprise contacting the hydrogel according to the third aspect with the at least one cell. The nature of step (ii) of the method will be determined by whether the composition in step (i) is a non-cross-linked solution or a cross-linked hydrogel.

The method may comprise exposing the hydrogel precursor composition to conditions such that a hydrogel is formed in step (i) prior to contacting the at least one cell therewith. Such conditions may comprise lowering the temperature of the composition to below the critical gelation temperature, e.g. less than about 39° C., and/or adding a suitable oxidising agent to allow cross-linking to occur.

In an alternative embodiment, the composition may be initially maintained under conditions in which it is in the form of the solution of non-cross-linked hydrogel precursor composition in step (i) of the method, to which the at least one cell is added in step (ii). Hence, the method may comprise initially exposing the composition in step (i) to conditions in which it is a solution (i.e. not a hydrogel). For example, the composition may be exposed to a pH or temperature or ionic strength at which the composition is non-cross-linked and therefore substantially liquid. The method may then comprise the step of contacting the at least one cell with the aqueous in step (i). After step (i), step (ii) preferably comprises exposing the liquid precursor composition to conditions in which it forms a hydrogel by forming cross-links between the PAA chains.

The hydrogel which forms, in which the at least one cell is supported, is referred to as the cell-supporting medium or cell scaffold.

In another embodiment, the cell-supporting medium may be prepared remote from the wound (eg. in the lab), and is then preferably administered to the area to be treated. In this approach, the gel would be formed in a pre-determined three-dimensional shape for example, by using a mould, and cells may either be added prior to the gelation process or after the gel has formed. The pre-formed gel may then be implanted in the body where the patient's cells migrate into the gel scaffold. Examples of this use would be in tissues, which have a migratory capacity and/or those, which are responsible for tissue remodelling. Examples are skin, bone, and peripheral nerves. The implant may also be supplemented with further cells externally by the medical practitioner. In addition, other factors, which may simulate cell and preferably tissue growth, may be added to the implant, for example, growth factors.

Preferably, the cell supporting medium or hydrogel, whether prepared in situ in the area to be treated, or remote from it, is suitably maintained to allow the at least one cell to divide to form a culture or tissue therein. Accordingly, it will be appreciated that the hydrogel acts as a supporting scaffold for the tissue and thereby allows repair of the wound, or regeneration of the damaged tissue.

The inventors believe that the method according to the twelfth aspect, may be used in wide variety of different, medical treatment methods, such as tissue regeneration/engineering applications, and in wound healing. The types of tissues and wound which could be treated are varied, and hence, it will be appreciated that the invention is not limited to any specific type of cell, which could be supported and cultured on the hydrogel administered to the treatment site. However, by way of example, suitable cells, which may be supported in the hydrogel include epithelial cells (e.g., hepatocytes), neurons, endothelial cells, osteoblasts (bone cells), chondrocytes (cartilage cells), fibroblasts, smooth muscle cells, osteoclasts, keratinocytes, nerve progenitor cells, Schwann cells, stem cells, macrophages, islet cells, and tumour cells, etc.

The cell type contacted with the composition or cell-supporting medium will depend on the type of wound being repaired, or the type of tissue being regenerated. Therefore, by way of example, if the wound is in skin, then at least one skin cell may be contacted with the hydrogel, composition or cell-supporting medium. If the wound is in bone, then at least one bone cell or osteoblast is preferably contacted with the hydrogel, composition or cell-supporting medium. If the wound is in cartilage, then at least one chondrocyte is preferably contacted with the hydrogel, composition or cell-supporting medium. If the eye tissue has been damaged, it may be required to contact the hydrogel, composition or cell-supporting medium with eye stem cells. It will be appreciated that different types of cell type may be contacted with the hydrogel, composition, or cell supporting medium, if necessary.

The compositions, hydrogel or cell supporting medium may be combined in formulations having a number of different forms depending, in particular on the manner in which the formulation is to be used. It will be appreciated that the vehicle of the composition of the invention should be one which is well-tolerated by the subject to whom it is given, and preferably enables efficient delivery of the composition to a target site. Thus, for example, the composition may be in the form of a liquid (i.e. the composition according to the first aspect), or a hydrogel (i.e. the composition according to the third aspect), or any other suitable form that may be administered to a person or animal.

The compositions, hydrogel, carrier particle, cell-supporting medium, or medicament according to the invention may be used in a monotherapy (i.e. use of the compositions, hydrogel, carrier particle, cell-supporting medium/scaffold, or medicament alone). Alternatively, the compositions, hydrogel, carrier particle, cell-supporting medium/scaffold, or medicament according to the invention may be used as an adjunct, or in combination with other known therapies.

In some circumstances, the compositions, hydrogel, carrier particle, cell-supporting medium/scaffold, or medicament according to the invention may be administered by injection into the wound areas. Injections may be intravenous (bolus or infusion) or subcutaneous (bolus or infusion).

Alternatively, the compositions, hydrogel, carrier particle, cell-supporting medium/scaffold, or medicament may also be incorporated within a slow or delayed release device. Such devices may, for example, be positioned on or adjacent the area to be treated, for example by implantation, and the compositions, hydrogel, carrier particle, cell-supporting medium/scaffold, or medicament may be released over weeks or even months. Such devices may be particularly advantageous when long-term treatment with the medicament is required and which would normally require frequent administration (e.g. at least daily injection or implant).

It will be appreciated that the amount of compositions, hydrogel, carrier particle, cell-supporting medium/scaffold, or medicament according to the invention required will be determined by its biological activity and bioavailability, which in turn depends on the mode of administration, the physicochemical properties of the medicament employed, and whether the compositions, hydrogel, carrier particle, cell-supporting medium/scaffold, or medicament is being used as a monotherapy or in a combined therapy. The frequency of administration will also be influenced by the above-mentioned factors and particularly the half-life of the medicament within the subject being treated.

Optimal dosages to be administered may be determined by those skilled in the art, and will vary with the particular medicament in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the medicament according to the invention, and precise therapeutic regimes (such as daily doses and the frequency of administration).

Generally, a daily dose of between 0.01 µg/kg of body weight and 1.0 g/kg of body weight of the hydrogel according to the invention may be used for the prevention and/or treatment of the specific medical condition. More preferably, the daily dose is between 0.01 mg/kg of body weight and 100 mg/kg of body weight. Daily doses may be given as a single administration (e.g. a single daily tablet). Alternatively, the medicament may require administration twice or more times during a day. As an example, the medicament according to the invention may be administered as two (or more depending upon the severity of the condition) daily doses of between 25 mg and 5000 mg. A patient receiving treatment may take a first dose upon waking and then a second dose in the evening (if on a two dose regime) or at 3 or 4 hourly intervals there-after. Alternatively, a slow release device may be used to provide optimal doses to a patient without the need to administer repeated doses.

In a fifteenth aspect, there is provided a pharmaceutical composition comprising a therapeutically effective amount of a composition according to the first or fifth aspect, the hydrogel according to the third aspect, or the carrier particle according to the seventh aspect; and a pharmaceutically acceptable excipient.

The invention also provides in a sixteenth aspect, a process for making the pharmaceutical composition according to the fifteenth aspect, the process comprising combining a therapeutically effective amount of a composition, hydrogel, or carrier particle according to the present invention; and a pharmaceutically acceptable excipient.

The pharmaceutical composition may comprise a cell supporting medium/scaffold according to the thirteenth aspect.

A "therapeutically effective amount" is any amount which, when administered to a subject provides prevention and/or treatment of a specific medical condition. A "subject" may be a vertebrate, mammal, domestic animal or human being.

A "pharmaceutically acceptable vehicle" as referred to herein is any physiological vehicle known to those of ordinary skill in the art useful in formulating pharmaceutical compositions. The pharmaceutically acceptable vehicle may be a liquid, and the pharmaceutical composition is in the form of a solution. In a further preferred embodiment, the pharmaceutical vehicle is a gel or hydrogel, and the composition is in the form of a cream or the like. In both cases, the composition may be applied to the treatment site.

The amount of the composition, hydrogel, carrier particle, or cell-supporting medium/scaffold may be from about 0.01 mg to about 800 mg. Preferably, the amount of the composition, hydrogel, carrier particle, or cell-supporting medium/scaffold is from about 0.01 mg to about 500 mg, more preferably, about 0.01 mg to about 250 mg, even more preferably, from about 0.1 mg to about 60 mg, and most preferably, from about 0.1 mg to about 20 mg.

The pharmaceutical composition may comprise one or more substances, which may also act as lubricants, solubilisers, suspending agents, fillers, glidants, compression aids, or binders. It may also be an encapsulating material. Liquid vehicles are used in preparing solutions, suspensions, emulsions, syrups, elixirs and pressurized compositions. The composition, hydrogel, carrier particle, or cell-supporting medium/scaffold or medicament according to the invention may be dissolved or suspended in a pharmaceutically acceptable liquid vehicle such as water, an organic solvent, a mixture of both or pharmaceutically acceptable oils or fats. The liquid vehicle may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration and implants include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

In cases where it is desired to inject or implant the composition, hydrogel, carrier particle, or cell-supporting medium/scaffold or medicament according to the invention directly to the treatment site, liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The composition, hydrogel, carrier particle, or cell-supporting medium/scaffold or medicament according to the invention may be prepared as a sterile composition that may be dissolved or suspended at the time of administration using sterile water, saline, or other appropriate sterile injectable medium. Vehicles are intended to include necessary and inert binders, suspending agents, lubricants, sweeteners, preservatives, dyes, and coatings.

It is preferred that the composition, hydrogel, carrier particle, or cell-supporting medium/scaffold or medicament according to the invention may be implanted in the form of a sterile solution or suspension or gel or hydrogel containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. Preferably, the composition, hydrogel, carrier particle, or cell-supporting medium/scaffold or medicament according to the invention is implanted either in liquid or solid (hydrogel) composition form. Compositions suitable for implants include liquid forms, such as solutions, syrups, elixirs, and suspensions.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which.

Figure 1:
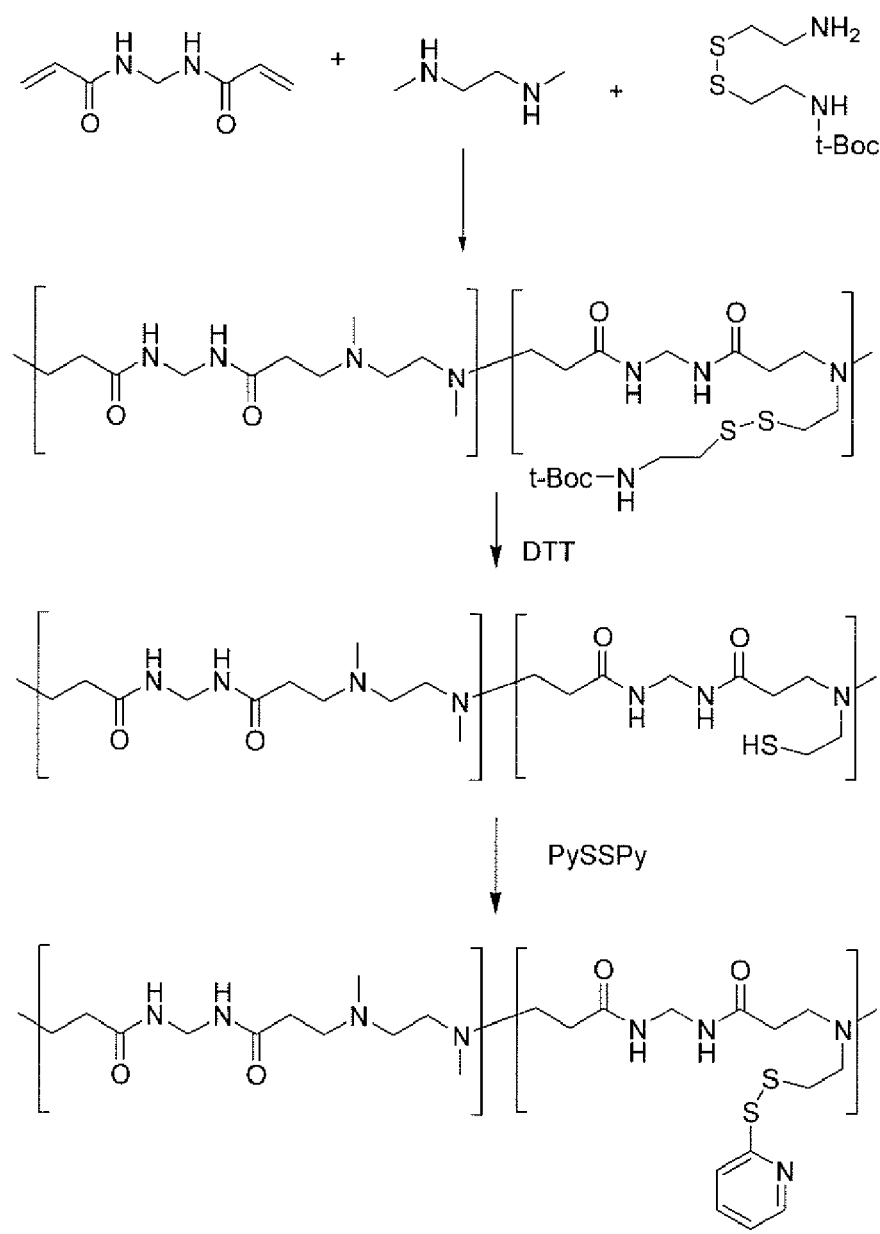
FIG. 1 depicts reaction Scheme 1. Scheme 1 shows a chemical reaction scheme for the preparation of polyamidoamine (PAA) containing pendant sulphydryl moieties.
Figure 2:
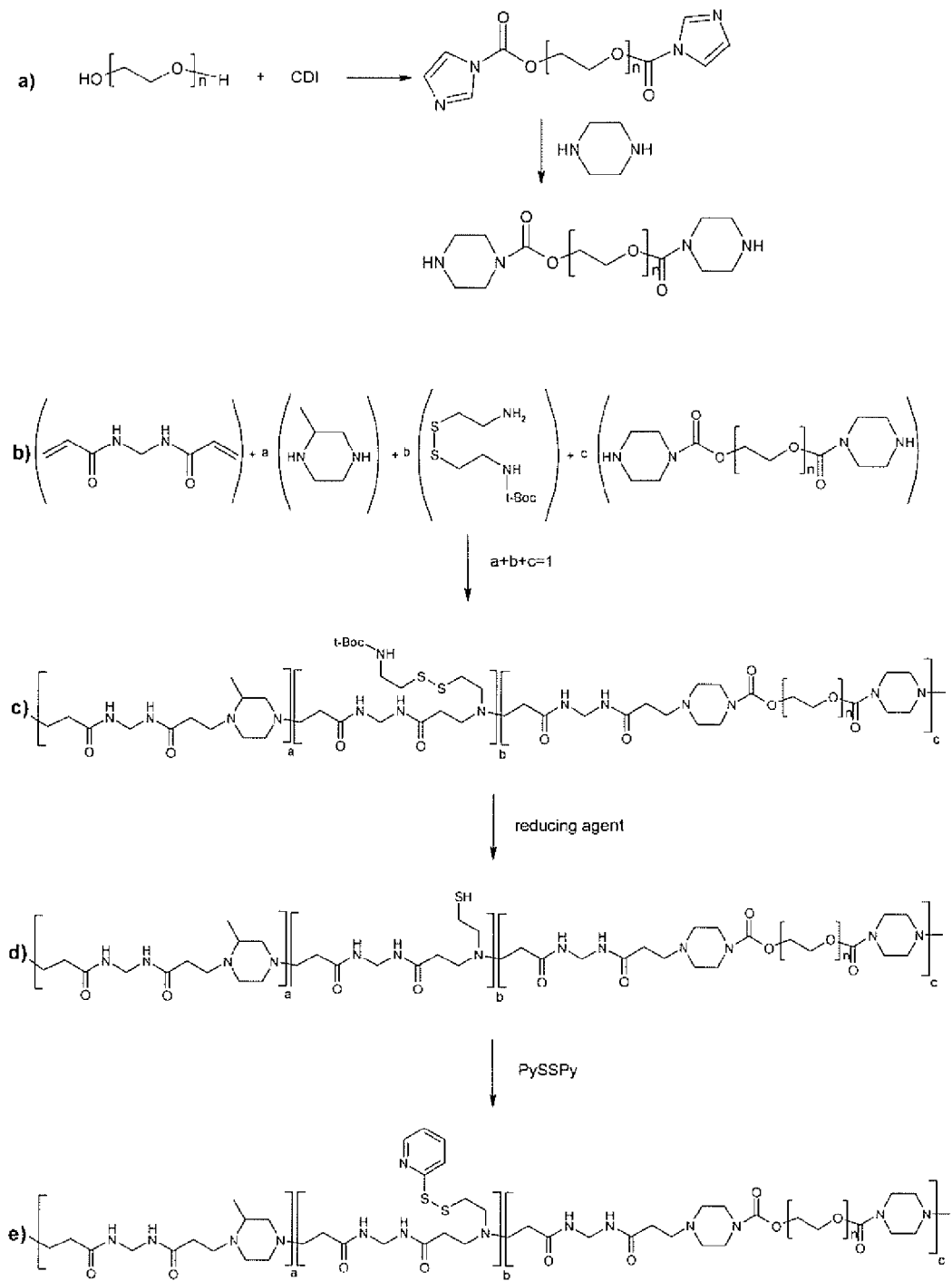
FIG. 2 depicts reaction Scheme 2. Scheme 2 shows a chemical reaction scheme for the preparation of cross-linkable PEG-PAAs to give multiblock linear PEG-PAA.
Figure 3:
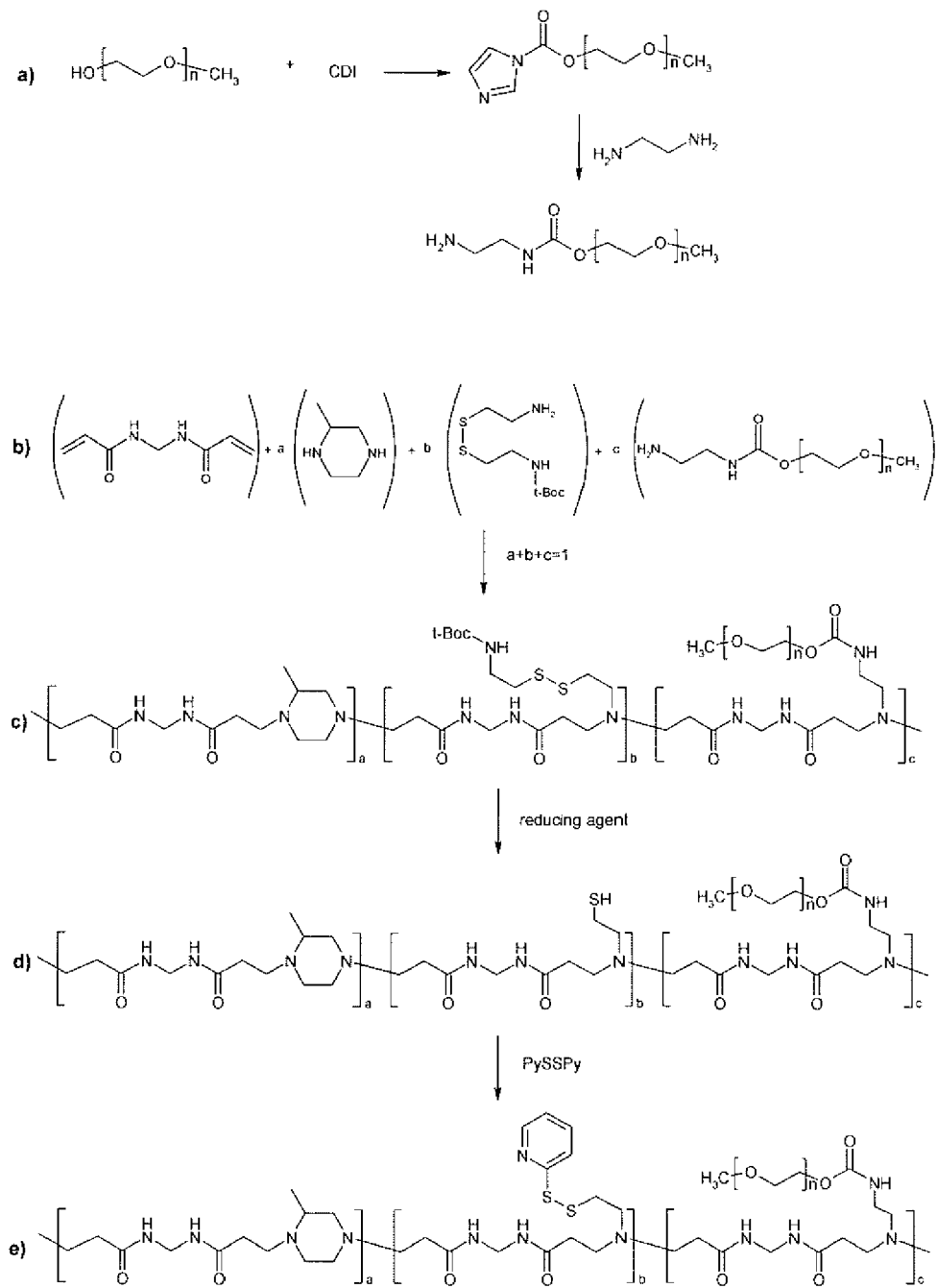
FIG. 3 depicts reaction Scheme 3. Scheme 3 shows a chemical reaction scheme for the preparation of cross-linkable PEG-PAA comb co-polymers.
Figure 4:
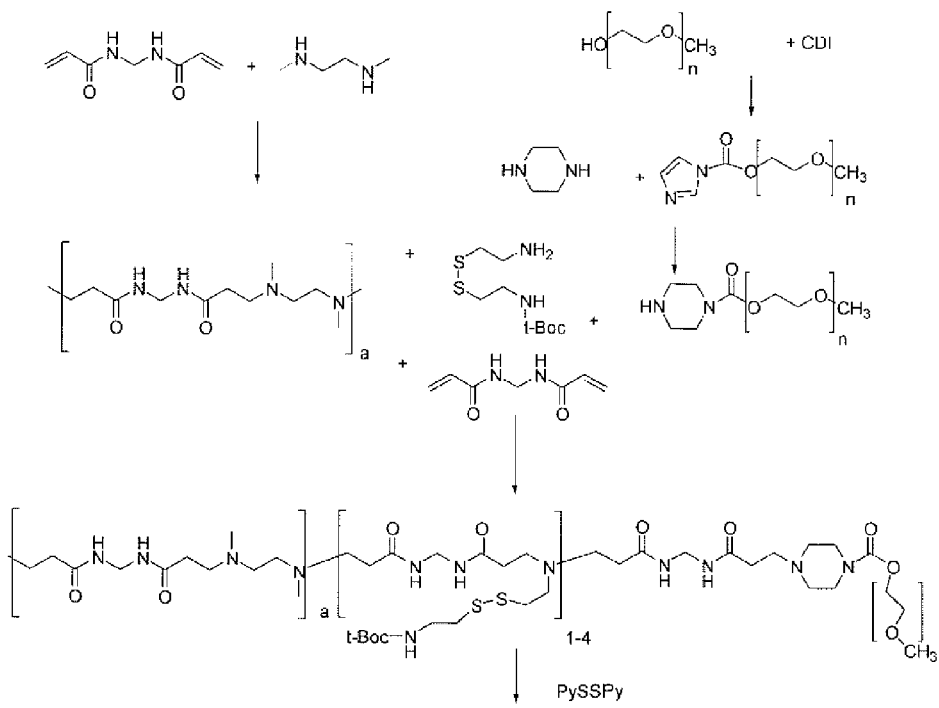
FIG. 4 depicts reaction Scheme 4. Scheme 4 shows a chemical reaction scheme for the preparation of PEG terminated PAA with block of pendant sulphydryl groups.
Figure 4:
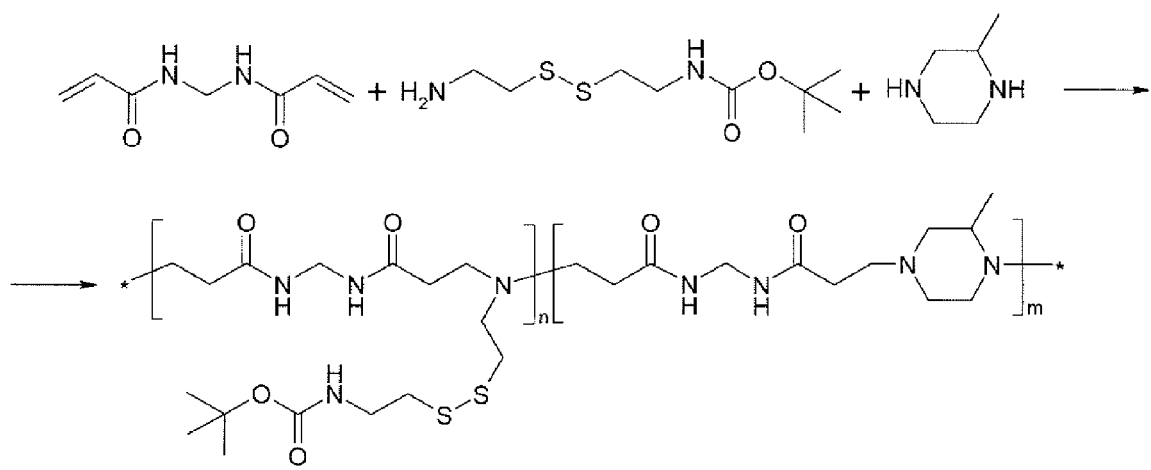
Figure 5:
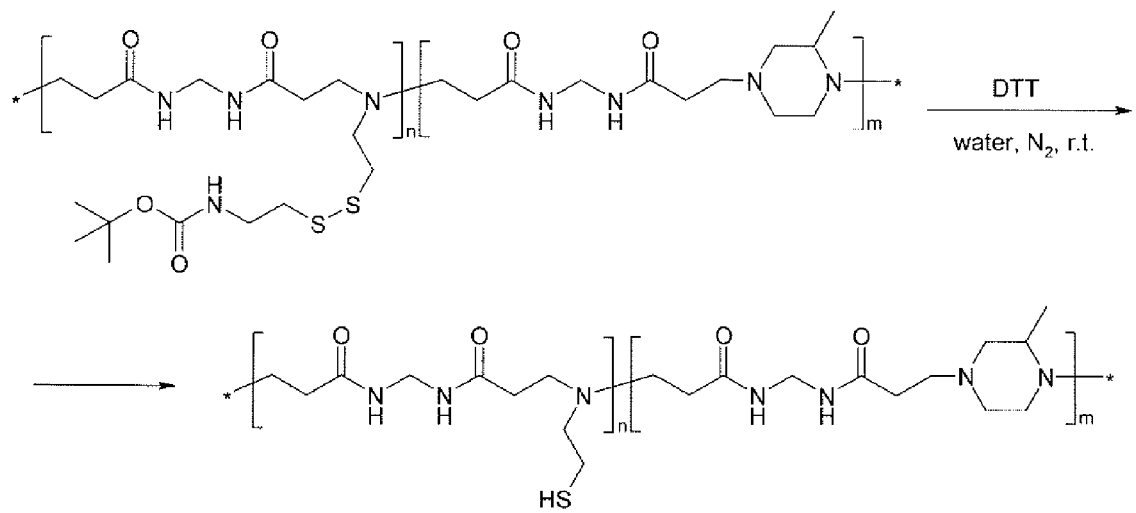
Figure 5:
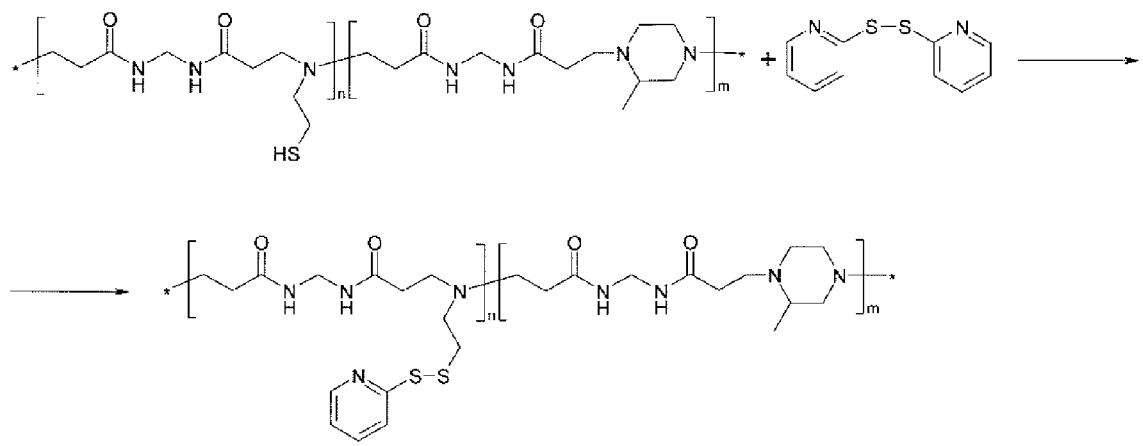
Figure 6:
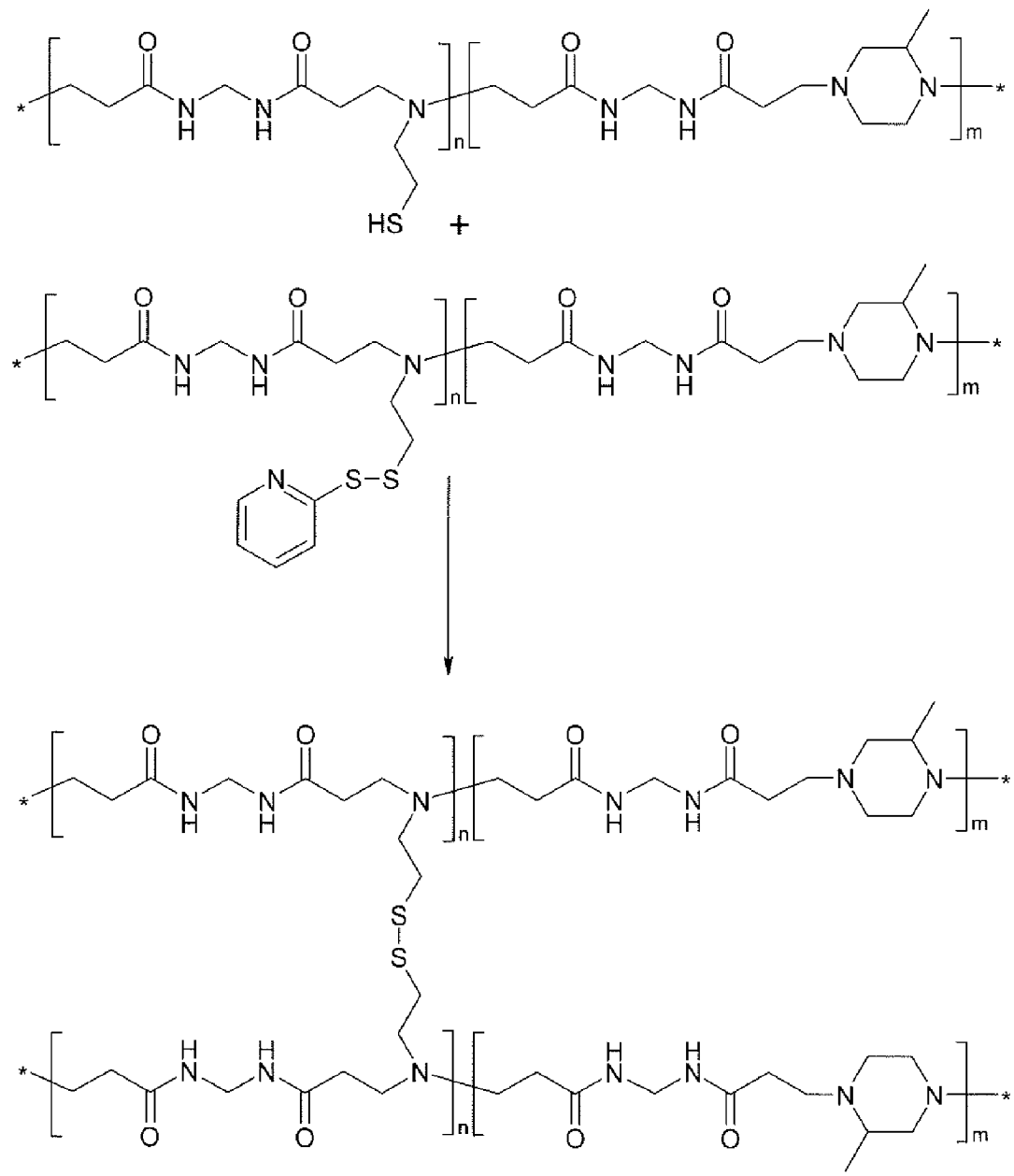
Figure 7:
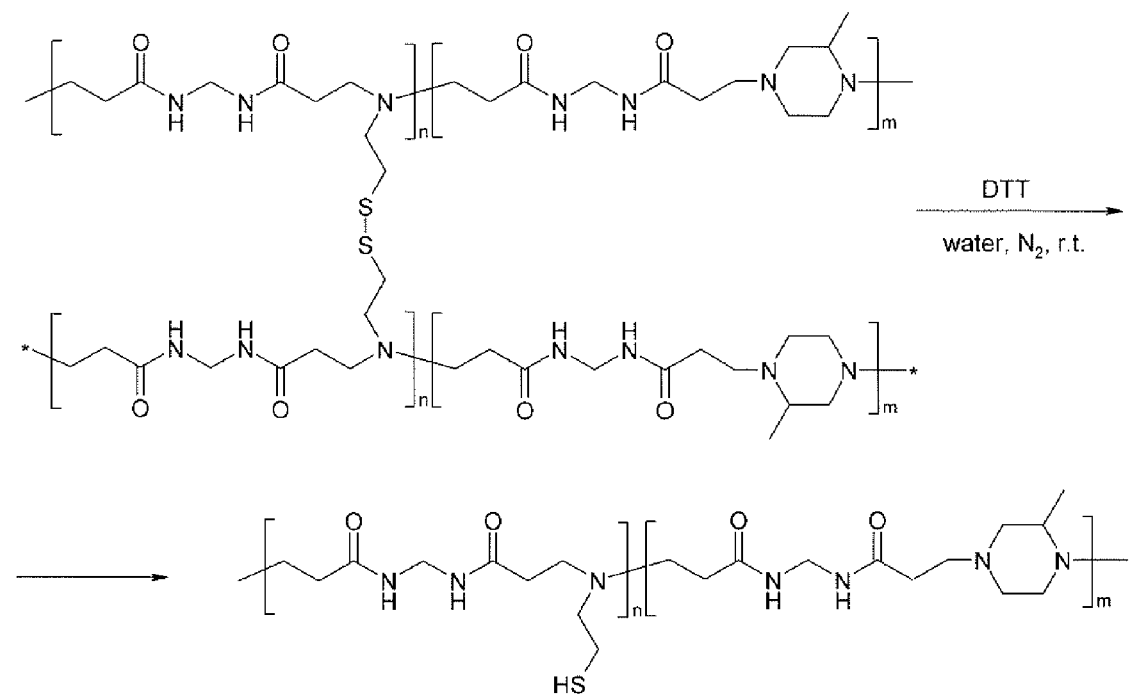
Figure 8:
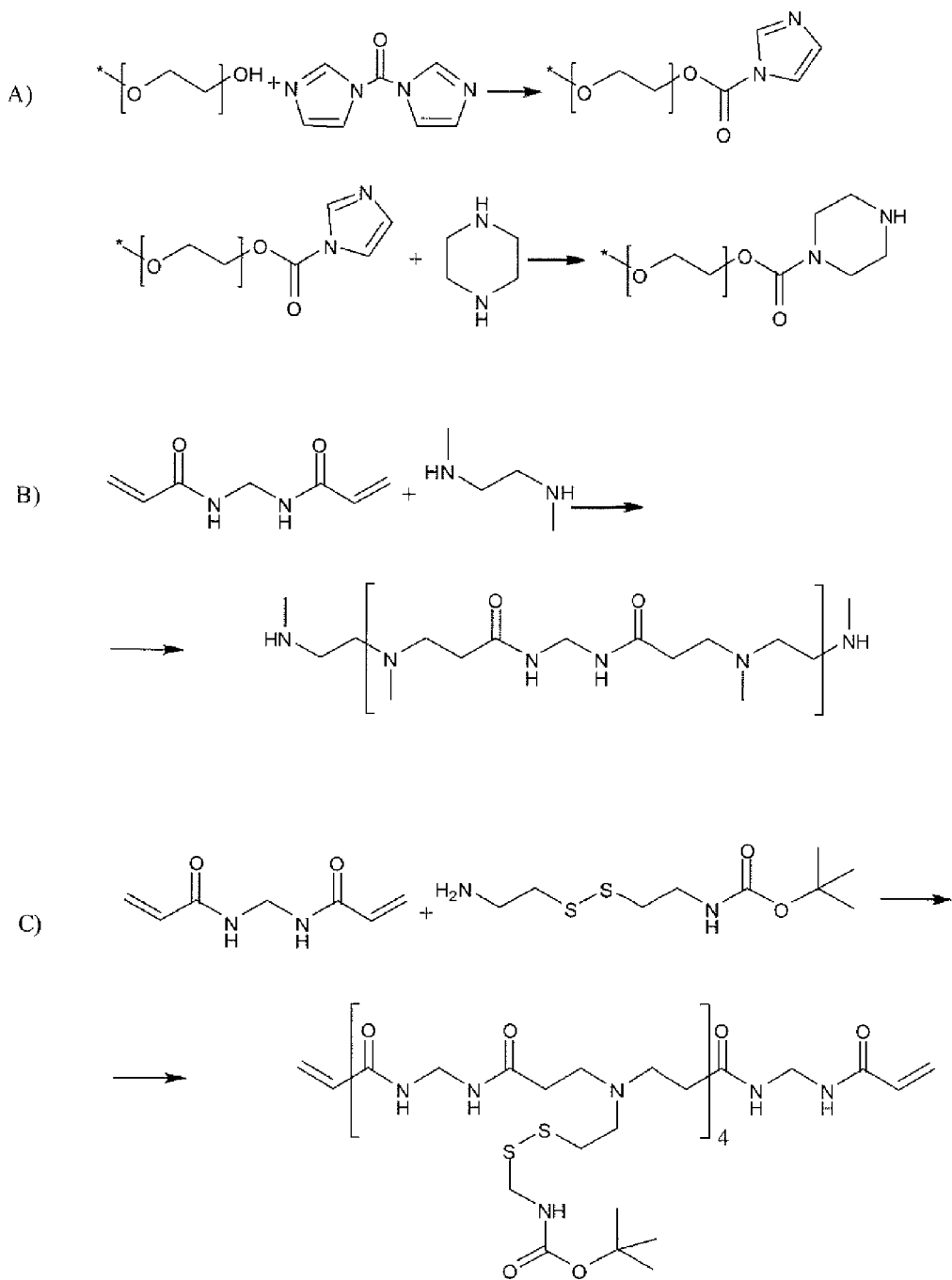
Figure 9:
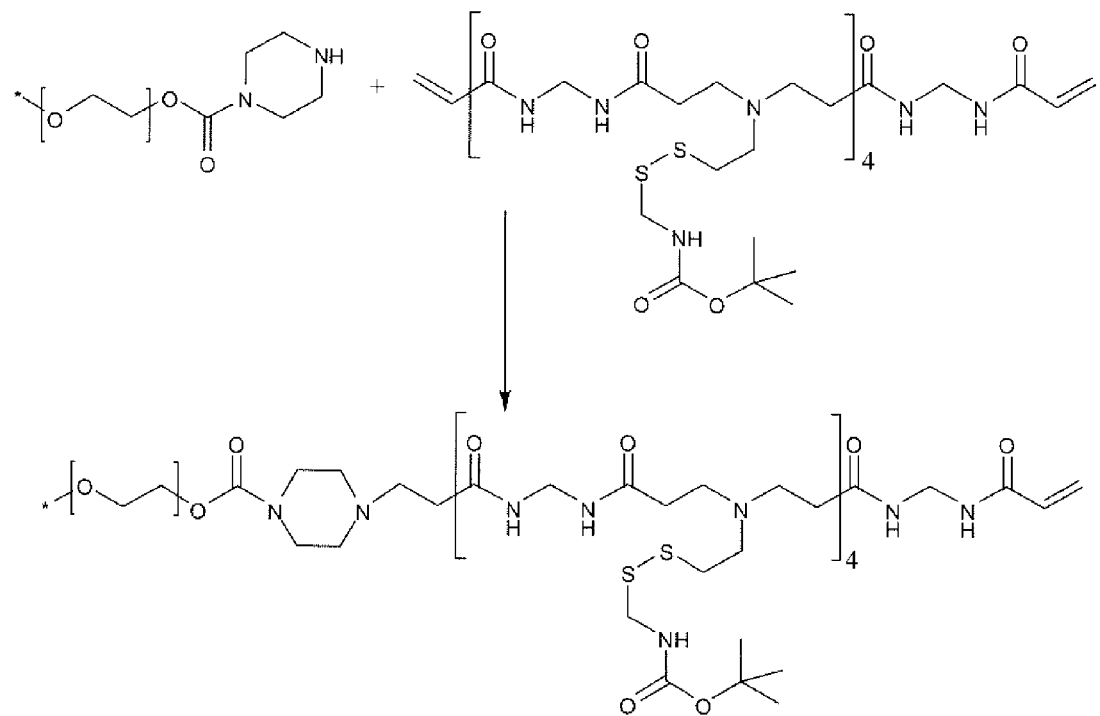
Figure 9:
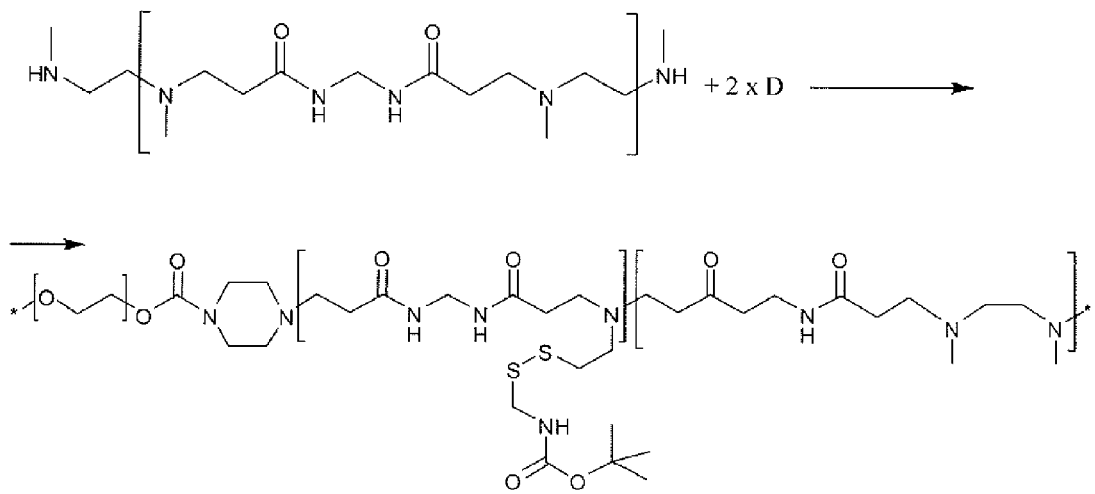
Figure 10:
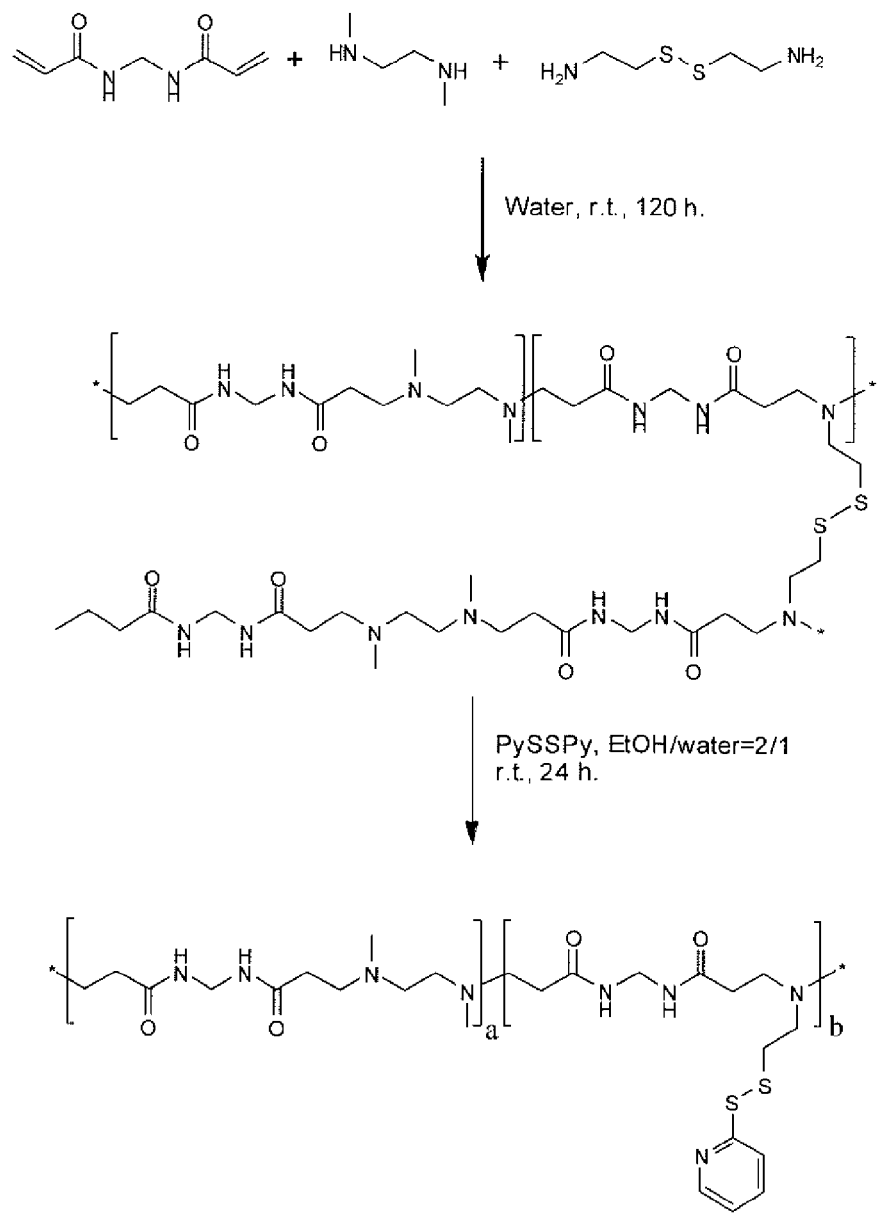
Figure 11:
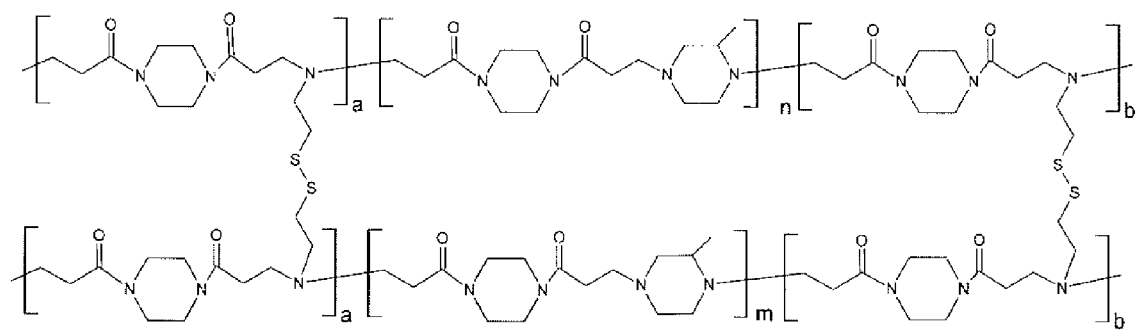
Figure 12:
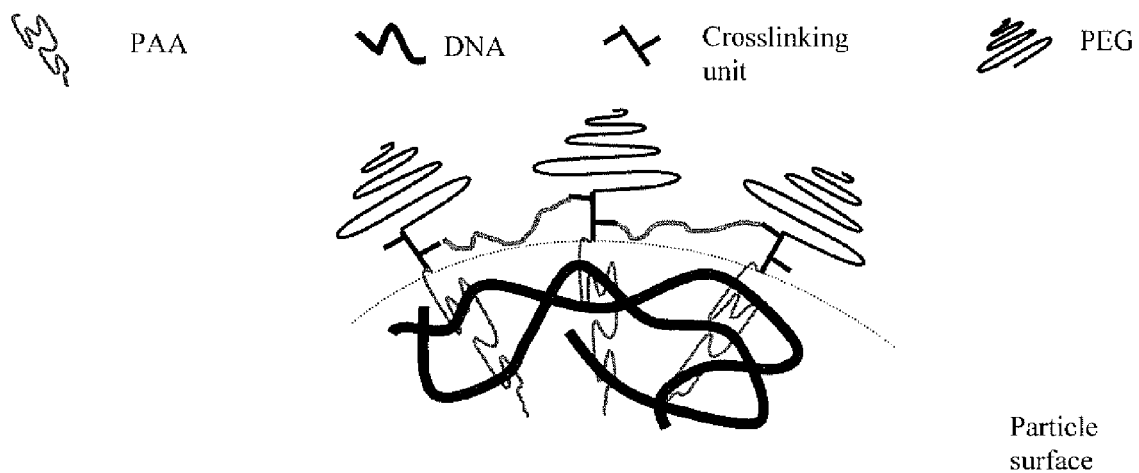
Figure 13:
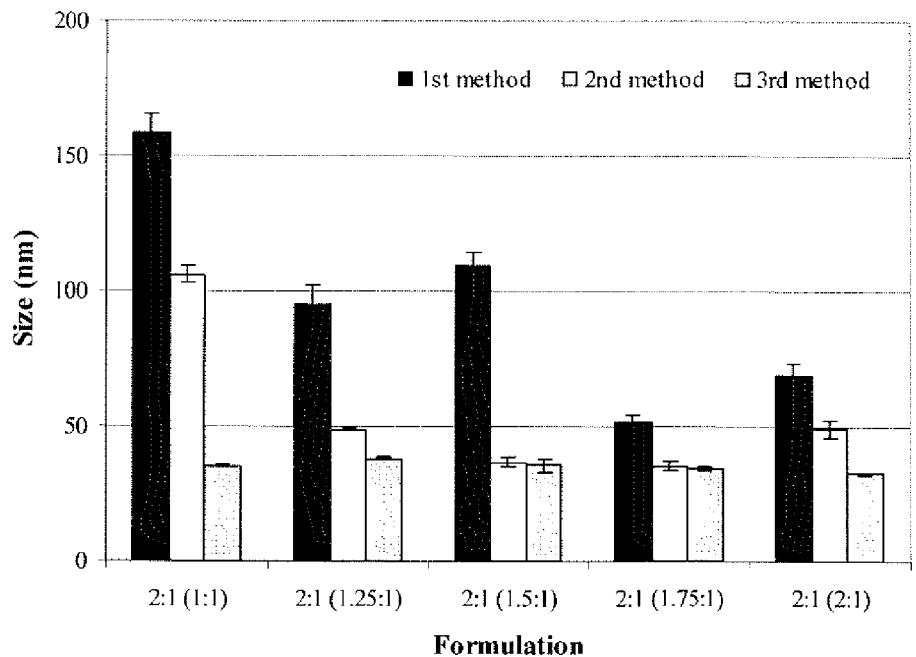
Figure 14:
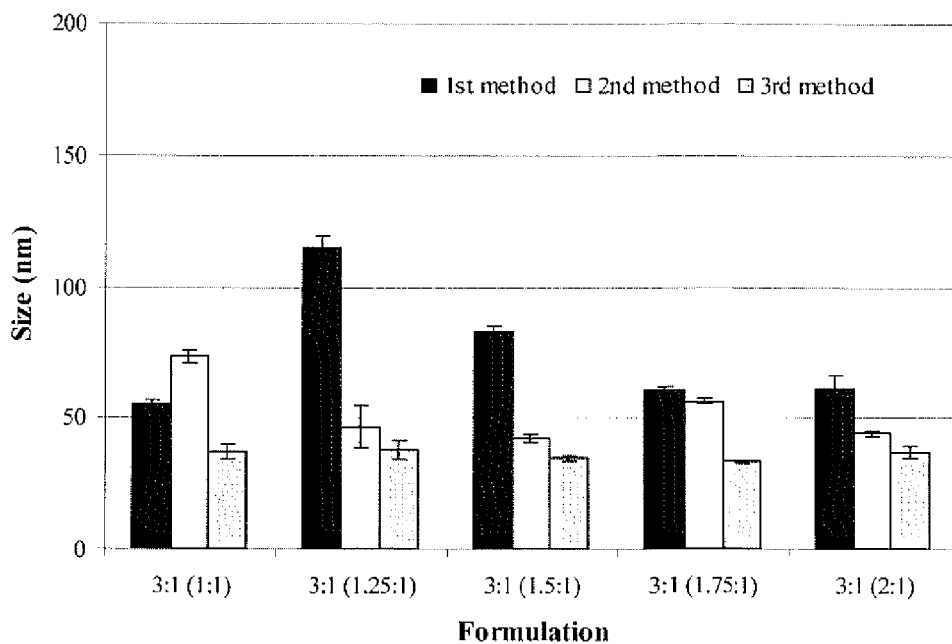
Figure 15:
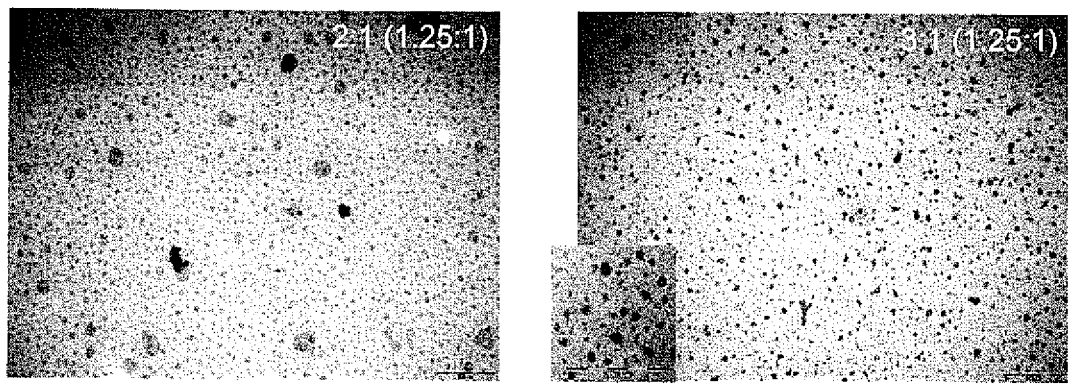
Figure 16:
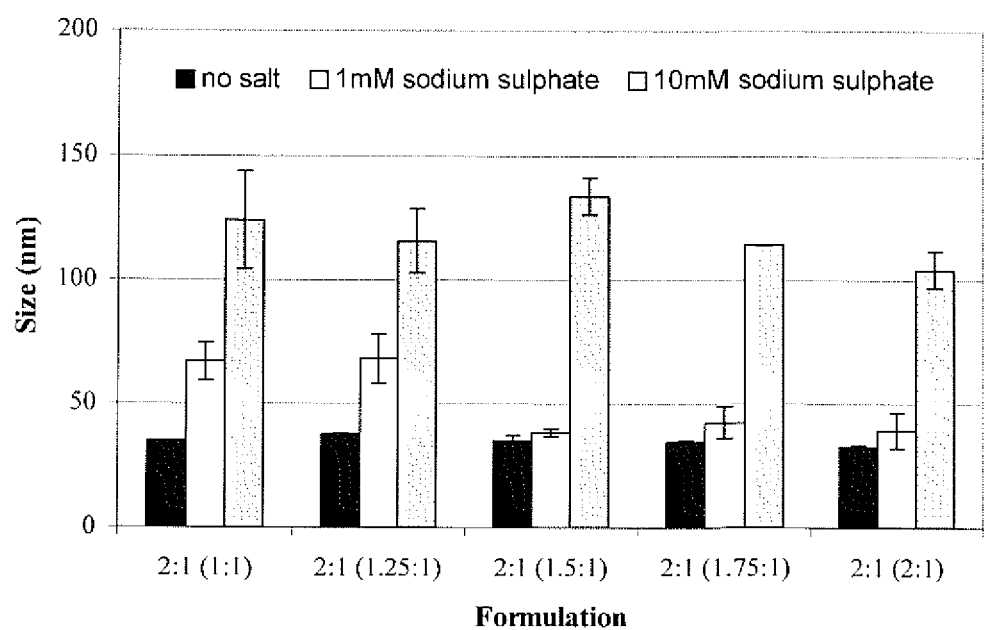
Figure 17:
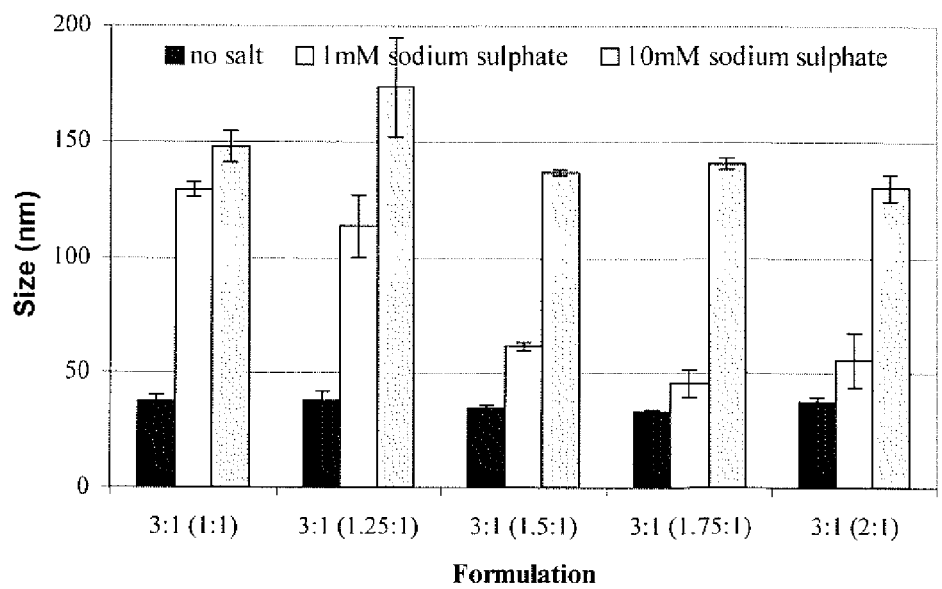
Figure 18:
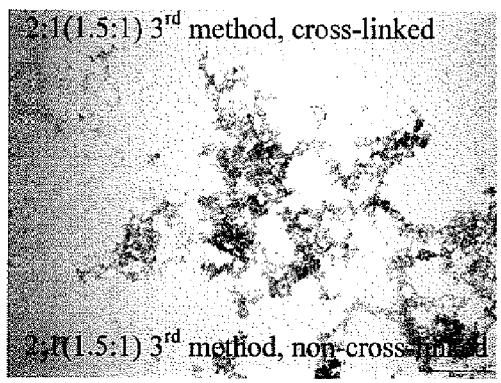
Figure 18:
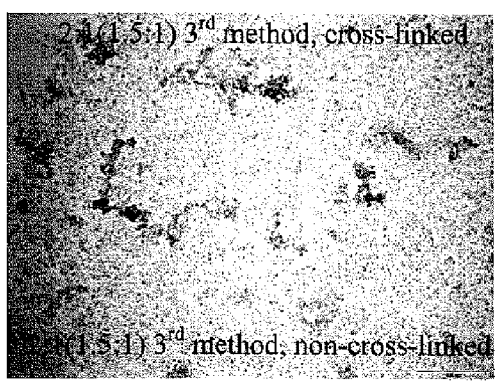
Figure 18:
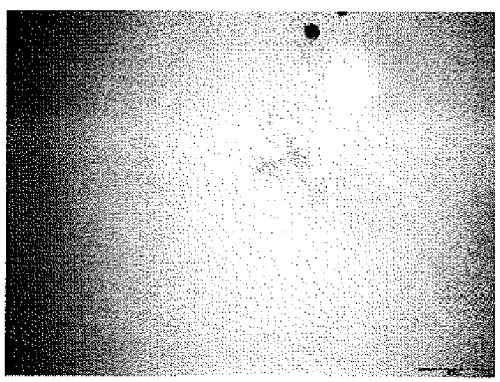
Figure 18:
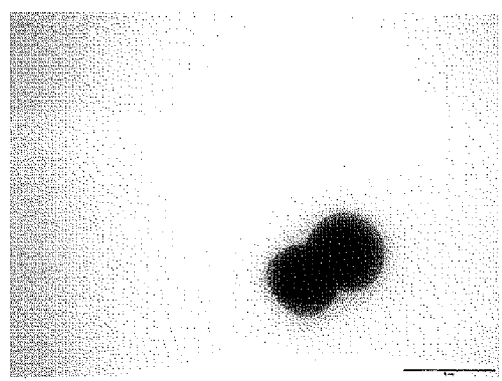
Figure 18:
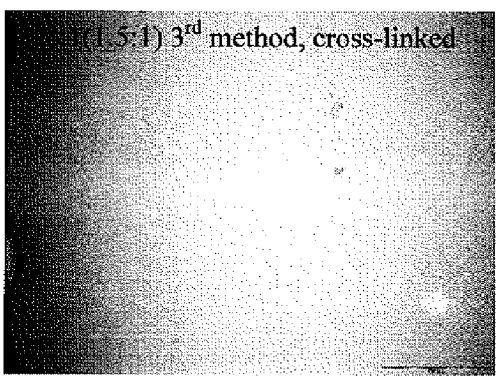
Figure 18:
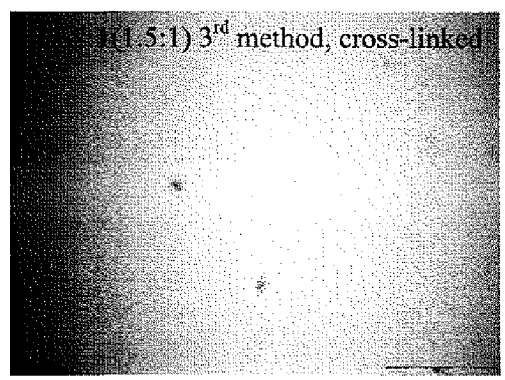
Figure 18:
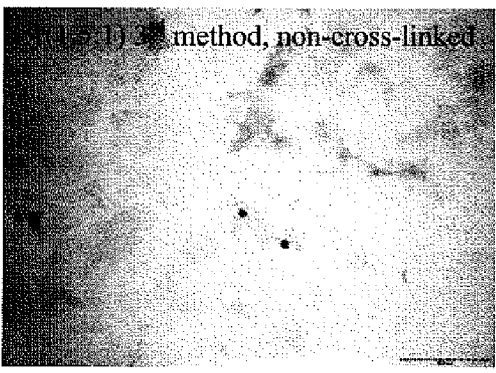
Figure 18:
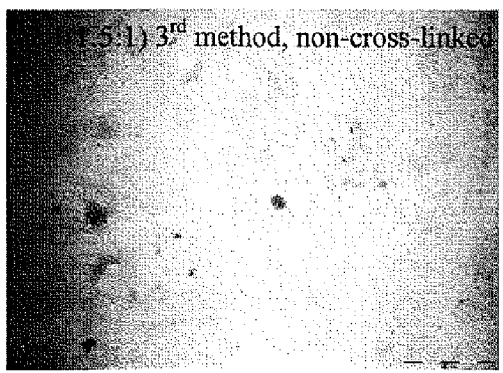
Figure 19:
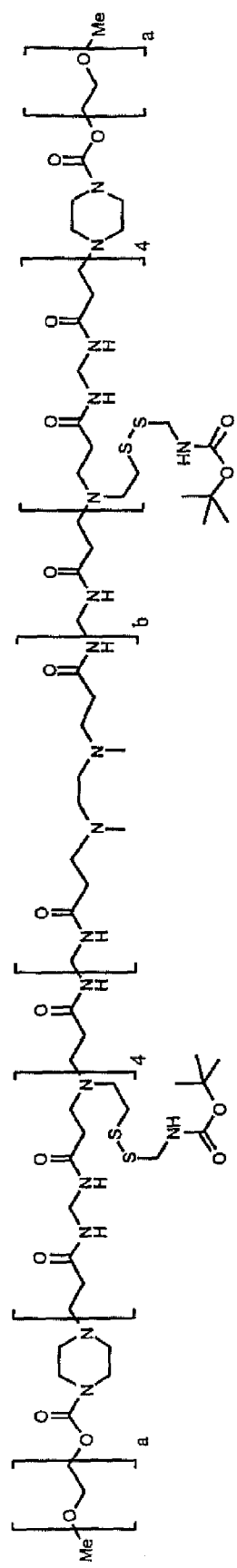

FIG. 4 also depicts reaction Scheme 5. Scheme 5 shows a chemical reaction scheme for preparing a polyamidoamine containing cystamine residues;

FIG. 5 depicts reaction Scheme 6. Scheme 6 shows a chemical reaction scheme for reducing Boc protected cystamine containing polymers to give a free sulphydryl group;

FIG. 5 also depicts reaction Scheme 7. Scheme 7 shows a chemical reaction scheme for activating free sulphydryl groups by thiol disulphide interchange with bipyridyl disulphide;

FIG. 6 depicts reaction Scheme 8. Scheme 8 shows a chemical reaction scheme for the formation of hydrogel by reaction of polymers containing a reduced thiol and polymers containing an activated thiol;

FIG. 7 depicts reaction Scheme 9. Scheme 9 shows a chemical reaction scheme for reduction of hydrogels to their component polymers;

FIG. 8 depicts reaction Scheme 10. Scheme 10 shows a chemical reaction scheme for the syntheses of Complexing Polymer (CP) precursors;

FIG. 9 depicts reaction Scheme 11. Scheme 11 shows a chemical reaction scheme for the general synthesis of CP polymers;

FIG. 10 depicts reaction Scheme 12. Scheme 12 shows a chemical reaction scheme for the synthesis of Cross-Linking Polymers (XLP);

FIG. 11 shows the chemical structure of a hydrogel consisting of PAAs cross-linked together by means of bonds formed between pendant sulphydryl groups;

FIG. 12 shows a schematic of cross-linking in polyelectrolyte complexes to form a DNA delivery nanoparticle;

FIG. 13 is a barchart showing particle sizes of 2:1 MBA/DMEDA25-Py to PEG-MBA/DMEDA16-SH-PEG ratio using different PAA:DNA ratios;

FIG. 14 Is a barchart showing particle sizes of 3:1 MBA/DMEDA25-Py to PEG-MBA/DMEDA16-SH-PEG ratio using different PAA:DNA ratios;

FIG. 15 shows representative images of complexes produced with a 2:1 MBA/DMEDA25-Py to PEG-MBA/DMEDA16-SH-PEG ratio and a 1.25:1 PAA:DNA ratio and with a 3:1 MBA/DMEDA25-Py to PEG-MBA/DMEDA16-SH-PEG ratio and a 1.25:1 PAA:DNA ratio are displayed in FIG. 15. Toroidal particles were formed having a size of 35 nm and 20 nm respectively;

FIG. 16 is a barchart showing particle sizes of 2:1 MBA/DMEDA25-Py to PEG-MBA/DMEDA16-SH-PEG ratio using different PAA:DNA ratios and made using the 3rd method before and after adding sodium sulphate;

FIG. 17 is a barchart showing particle sizes of 3:1 MBA/DMEDA25-Py to PEG-MBA/DMEDA16-SH-PEG ratio using different PAA: DNA ratios and made using the 3rd method before and after adding sodium sulphate;

FIG. 18 are TEM images of solution left on filter or filtrate after spinning the complexes on a centrifugal ultrafilter. Complexes used are a 2:1 MBA/DMEDA25-Py to PEG-MBA/DMEDA16-SH-PEG ratio using 1.5:1 PAA:DNA ratio and a 2:1 MBA/DMEDA25-Py to PEG-MBA/DMEDA16-Cys-PEG ratio using a 1.5:1 PAA:DNA ratio; and FIG. 19 shows the general structure of Complexing Polymers (CP)—CP03: a=16, b=15; CP04: a=16, b=48; CP05: a=45, b=48; CP06: a=45, b=15.

EXAMPLES

Example 1

Polymerisation of methylene bisacrylamide (MBA) with 2-methyl-piperazine (MP) and Boc-cystamine (30%) (MBA30-cyst). In a round bottomed flask, equipped with a magnetic stirrer and nitrogen inlet, MBA (100.2 g, 0.65 mol) was dissolved under inert atmosphere in distilled water (200 mL). Boc-cystamine (49.2 g, 0.195 mol) was added and allowed to react for 6 hours. Then MP (45.6 g, 0.455 mol) was added and the reactive solution was allowed to react under stirring, protected from direct light. After 72 hours the viscous solution was diluted with a 1.0 M HCl aqueous solution down to pH 5.0, ultrafiltered through a membrane of 5,000 nominal cut-off and lyophilized. The product was isolated as hydrochloride salt. Yield 176.5 g, 85% $\overline{M}_n$=25700; $\overline{M}_w$=49200.

Example 2

Polymerisation of BP with MP and Boc-cystamine (30%) (BP30-cyst). The same procedure described in Example 1 was followed, but using BP (126.3 g, 0.65 mol) for MBA, the quantities of the other reagents being the same. The product was isolated in the same way. Yield: 190.7 g (73.0%). $\overline{M}_n$=23800; $\overline{M}_w$=47000.

Example 3

Polymerisation of BP with MP and Boc-cystamine(50%) (BP50-cyst). The same procedure described in Example 2, but using a different amount of Boc-cystamine (82.0 g, 0.325 mol) and of MP (45.6 g, 0.325 mol), the quantities of the other reagents being the same. The product was isolated in the same way. Yield: 209.4 g (75.8%). $\overline{M}_n$=21500; $\overline{M}_w$=41700.

Example 4

Reduction of MBA30-cyst with DTT (MBA30-SH-a). In a round bottomed flask, equipped with a magnetic stirrer and nitrogen inlet, MBA30cyst (100 g, 0.083 mol of Boc-cystamine pendants) was dissolved under inert atmosphere in distilled water (500 mL). pH was adjusted to 8.5 with NaOH and a three-fold excess of DTT was added (38.3 g, 0.25 mmol). The reactive solution was allowed to react for 6 hours. It was diluted with a 1.0 M HCl aqueous solution down to pH 2, ultrafiltered through a membrane of 5,000 nominal cut-off using in de-oxygenated water and lyophilized. The product was isolated as hydrochloride salt and stored under nitrogen atmosphere. Yield 70.0 g (81.9%). $\overline{M}_n$=31600; $\overline{M}_w$=62500.

Example 5

Reduction of MBA30-cyst with $Na_2S_2O_5$ (MBA30-SH-b). The same procedure described in Example 2 was followed, but using $Na_2S_2O_5$ (47.3 g, 0.25 mol) for DTT, the quantities of the other reagents being the same. The product was isolated in the same way, but a lower pH (at least pH 2) was necessary to completely eliminate sulphurous acid. Yield: 71.8 g (84.0%). $\overline{M}_n$=33400; $\overline{M}_w$=67100.

Example 6

Reduction of BP30-cyst with DTT (BP30-SH-a). The same procedure described in Example 4 was followed, but using BP30-cyst (100 g, 0.075 mol Boc-cystamine pendants) for MBA30-cyst. A three-fold excess of DTT was used (34.5 g, 0.22 mmol), the other reaction conditions being the same. The product was isolated in the same way. Yield: 74.5 g (87.7%). $\overline{M}_n$=29000; $\overline{M}_w$=60700.

Example 7

Reduction of BP30-cyst with $Na_2S_2O_5$ (BP30-SH-b). The same procedure described in Example 6 was followed, but using $Na_2S_2O_5$ (42.6 g, 0.22 mol) for DTT. The product was isolated in the same way, but a lower pH (at least pH 2) was necessary to completely eliminate sulphurous acid. Yield: 69.5 g (80.0%). $\overline{M}_n$=26800; $\overline{M}_w$=50300.

Example 8

Reduction of BP50-cyst with DTT (BP50-SH-a). The same procedure described in Example 6 was followed, but using BP50-cyst (100 g, 0.118 mol Boc-cystamine pendants) for BP30-cyst. A three-fold excess of DTT was used (54.41 g, 0.35 mmol), the other reaction conditions being the same. The product was isolated in the same way. Yield: 65.1 g (82.0%). $\overline{M}_n$=23400; $\overline{M}_w$=25900.

Example 9

Reduction of BP50-cyst with $Na_2S_2O_5$ (BP50-SH-b). The same procedure described in Example 8 was followed, but using $Na_2S_2O_5$ (67.1 g, 0.35 mol) for DTT. The product was isolated in the same way, but a lower pH (at least pH 2) was necessary to completely eliminate sulphurous acid. Yield: 66.1 g (83.3%). $\overline{M}_n$=22800; $\overline{M}_w$=45300

Example 10

Thiol-disulphide exchange between MBA30-SH and bi-pyridyldisulphide (MBA30-Py). In a round bottomed flask, equipped with a magnetic stirrer and nitrogen inlet, MBA30-SH (50 g, 0.043 mol thiol functional groups) was dissolved under inert atmosphere in de-oxygenated TRIS buffer (100 mL, 0.1 M, pH 8.5). Bi-pyridyl disulphide (10.4 g, 0.047 mol) was added to the stirred solution, that became almost immediately yellow, due to the presence of 2-mercaptopyridine, and allowed to react for 15 hours. Subsequently the solution was diluted with a 1.0 M HCl aqueous solution down to pH 3.0, ultrafiltered through a membrane of 5,000 nominal cut-off and lyophilized. The product was isolated as hydrochloride salt. Yield 50.2 g, 91.8%. $\overline{M}_n$=30000; $\overline{M}_w$=58400.

Example 11

Hydrogel formation by thiol-activated disulphide exchange between MBA30-Py and MBA30-SH (HG-MBA30-a). In a round bottomed flask, equipped with a magnetic stirrer and nitrogen inlet, MBA30-Py (50 g, 0.039 mol activated disulphide groups) was dissolved under inert atmosphere in de-oxygenated TRIS buffer (80 mL, 0.1 M, pH 8.5). MBA30-SH (40.5 g, 0.039 mol of thiol functional groups) was added to the stirred solution that became almost immediately viscous and yellow. After half an hour, stirring was stopped and the reactive mixture was allowed to react for 15 hours. A solid transparent hydrogel was formed. It was ground, washed with 1.0 M HCl and several times with a 1:1 ethanol:water solution, till the washing liquors appeared no more coloured. The hydrogel was then washed three times with acetone and dried under vacuum to obtain a fine powder. Yield 81.2 g, 94.2%.

Referring to Scheme 8, there is shown the reaction scheme for the formation of a hydrogel by reaction of polymers containing a reduced thiol and polymers containing an activated thiol.

Example 12

Thiol-disulphide exchange between BP50-SH and bipyridyidisulphide (BP50-Py). The same procedure described in Example 10 was followed, but using BP50-SH (50 g, 0.0748 mol of thiol functional groups) for MBA30-SH, consequently changing the bi-pyridyldisulphide amount (17.9 g, 0.0814 mol), the other reaction condition being the same. The product was isolated in the same way. Yield: 51.4 g (88.5%). $\overline{M}_n$=19900; $\overline{M}_w$=40100

Example 13

Hydrogel formation by thiol-activated disulphide exchange between BP50-Py and BP50-SH. (HG-BP50-a) The same procedure described in Example 11 was followed, but using BP50-Py (50.0 g, 0.064 mol activated disulphide groups) for MBA30-Py and BP50-SH (43.1 g, 0.064 mol of thiol functional groups) for MBA30-SH, the other reaction conditions being the same. The product was isolated in the same way. Yield 81.7 g (95.0%)

Example 14

Hydrogel formation through oxidation of MBA30-SH by the air oxygen (HG-MBA30-b). In a round bottomed flask, equipped with a magnetic stirrer, MBA30-SH (50 g, 0.039 mol thiol functional groups) was dissolved in TRIS buffer (40 mL, 0.1 M, pH 8.5). When a clear solution was formed, it was transferred in a Petri dish and covered. After 48 hours a transparent gel was formed, similar in consistency and aspect to HG-MBA30-a obtained in Example 11. It was ground, washed with 0.1 M HCl and then several times with distilled water till the washing liquors appeared neutral. The hydrogel was then washed three times with acetone and dried under vacuum to obtain a fine powder. Yield 46.3 g, 92.7%.

Example 15

Hydrogel formation through oxidation of MBA30-SH by hydrogen peroxide (HG-MBA30-c). In a round bottomed flask, equipped with a magnetic stirrer, MBA30-SH (50 g, 0.039 mol thiol functional groups) was dissolved in TRIS buffer (30 mL, 0.1 M, pH 8.5). When a clear solution was formed, a hydrogen peroxide 5% solution in water (26.7 ml, 0.039 mol) was added and stirring was stopped after few minutes. Almost immediately the solution became more viscous then before. After 3 hours a transparent gel was formed, similar in consistency and aspect to HG-MBA30-a and HG-MBA30-a. It was ground, washed with 0.1 M HCl and then several times with distilled water till the washing liquors appeared neutral. The hydrogel was then washed three times with acetone and dried under vacuum to obtain a fine powder. Yield 47.4 g, 94.9%.

Example 16

Hydrogel formation through oxidation of BP30-SH by the air oxygen (HG-BP30-a). The same procedure described in Example 14 was followed, but substituting BP30-SH (50 g, 0.043 mol thiol functional groups) for MBA30-SH, the other reaction conditions being the same. The product was isolated in the same way. Yield 47.7 g, 95.6%.

Example 17

Hydrogel formation through oxidation of BP30-SH by hydrogen peroxide (HG-BP30-b). The same procedure described in Example 15 was followed, but substituting BP30-SH (50 g, 0.043 mol thiol functional groups) for MBA30-SH, consequently changing the hydrogen peroxide amount (29.2 g, 0.043 mol), the other reaction conditions being the same. The product was isolated in the same way. Yield 45.8 g, 91.8%.

Example 18

Hydrogel formation through oxidation of BP50-SH by the air oxygen (HG-BP50-b). The same procedure described in Example 14 was followed, but substituting BP50-SH (50 g, 0.064 mol thiol functional groups) for MBA30-SH, the other reaction conditions being the same. The product was isolated in the same way. Yield 46.1 g, 92.4%.

Example 19

Hydrogel formation through oxidation of BP50-SH by hydrogen peroxide (HG-BP50-c). The same procedure described in Example 15 was followed, but substituting BP50-SH (50 g, 0.064 mol thiol functional groups) for MBA30-SH, consequently changing the hydrogen peroxide amount (43.36 g, 0.064 mol), and the amount of TRIS buffer (20 ml), the other reaction conditions being the same. The product was isolated in the same way. Yield 46.9 g, 94.0%.

Example 20

Polymerisation of MBA with MP and cystamine (30%) (HG-MBA30-d). In a round bottomed flask, equipped with a magnetic stirrer and nitrogen inlet, MBA (100.2 g, 0.65 mol) was dissolved under inert atmosphere in distilled water (200 mL). Cystamine bis-hydrochloride (22.0 g, 0.0975 mol) was added with the stoichiometric amount of lithium hydroxyde monohydrate (8.18 g, 0.195 mol). When dissolution was complete, MP (45.6 g, 0.455 mol) was added, stirred for half an hour, and allowed to react under stirring, protected from direct light. After 120 hours a transparent gel was formed, similar in consistency and aspect to HG-MBA30-a obtained in Example 11. The hydrogel was ground, washed with 0.1 M HCl and then several times with distilled water till the washing liquors appeared neutral. The hydrogel was then washed three times with acetone and dried under vacuum to obtain a fine powder. Yield 46.3 g, 92.7%.

Example 21

Polymerisation of BP with MP and cystamine (30%) (HG-BP30-c). The same procedure described in Example 20 was followed, but using BP (126.3 g, 0.65 mol) for MBA, the quantities of the other reagents being the same. The product was isolated in the same way. Yield: 203.6 g (89.6%). Consistency and aspect were similar to HG-BP30-a obtained in Example 16.

Example 22

Polymerisation of BP with MP and cystamine (50%) (HG-BP50-d). The same procedure described in Example 21 was followed, but using a different amount of cystamine di-hydrochloride (36.6 g, 0.163 mol) and of MP (32.6 g, 0.325 mol), the quantities of the other reagents being the same. The product was isolated in the same way. Yield: 195.0 g (89.0%). Consistency and aspect were similar to HG-BP30-a obtained in Example 13.

Example 23

Reduction and dissolution of HG-MBA30-d with DTT (MBA30-SH-c). In a round bottomed flask, equipped with a magnetic stirrer and nitrogen inlet, HG-MBA30-d (100 g, 0.049 mol of cystamine groups) was allowed to swell under inert atmosphere in distilled water (500 mL). The pH was adjusted to 8.5 with NaOH and a three-fold excess of DTT was added (22.45 g, 0.15 mmol). The reactive solution was allowed to react for 6 hours. It was diluted with a 1.0 M HCl aqueous solution down to pH 2, ultrafiltered through a membrane of 5,000 nominal cut-off in de-oxygenated water, and finally lyophilized. The product was isolated as hydrochloride salt and stored under nitrogen atmosphere. Yield 73.1 g (73.2%). $\overline{M}_n$=32600; $\overline{M}_w$=63500.

Example 24

Reduction and dissolution of HG-MBA30-d with $Na_2S_2O_5$ (MBA30-SH-d). The same procedure described in Example 23 was followed, but using $Na_2S_2O_5$ (27.7 g, 0.15 mol) for DTT, the quantities of the other reagents being the same. The product was isolated in the same way, but a lower pH (at least pH 2) was necessary to completely eliminate sulphurous acid. Yield: 74.7 g (74.6%). $\overline{M}_n$=31400; $\overline{M}_w$=60200.

Example 25

Reduction and dissolution of HG-BP30-d with DTT (BP30-SH-c). The same procedure described in Example 23 was followed, but using HG-BP30-c (100 g, 0.043 mol cystamine groups) for HG-MBA30-d. A three-fold excess of DTT was used (19.9 g, 0.13 mmol), the other reaction conditions being the same. The product was isolated in the same way. Yield: 68.5 g (68.4%). $\overline{M}_n$=23400; $\overline{M}_w$=47200.

Example 26

Reduction and dissolution of HG-BP30-d with $Na_2S_2O_5$ (BP30-SH-d). The same procedure described in Example 25 was followed, but using $Na_2S_2O_5$ (24.5 g, 0.13 mol) for DTT, the quantities of the other reagents being the same. The product was isolated in the same way, but a lower pH (at least pH 2) was necessary to completely eliminate sulphurous acid. Yield: 71.9 g (71.8%). $\overline{M}_w$=31400; $\overline{M}_w$=60200.

Example 27

Reduction and dissolution of HG-BP50-d with DTT (BP50-SH-c). The same procedure described in Example 23 was followed, but using HG-BP30-c (100 g, 0.043 mol cystamine groups) for HG-MBA30-d. A three-fold excess of DTT was used (19.9 g, 0.13 mmol), the other reaction conditions being the same. The product was isolated in the same way. Yield: 68.5 g (68.4%). $\overline{M}_n$=23400; $\overline{M}_w$=47200.

Example 28

Reduction and dissolution of HG-BP30-d with $Na_2S_2O_5$ (BP30-SH-d). The same procedure described in Example 25 was followed, but using $Na_2S_2O_5$ (24.5 g, 0.13 mol) for DTT, the quantities of the other reagents being the same. The product was isolated in the same way, but a lower pH (at least pH 2) was necessary to completely eliminate sulphurous acid. Yield: 71.9 g (71.8%). $\overline{M}_n$=31400; $\overline{M}_w$=60200.

Example 29

Hydrogel formation through oxidation of MBA30-SH-d by the air oxygen (HG-MBA30-e). The same procedure described in Example 14, but substituting MBA30-SH-d for MBA30-SH-a, the other reaction condition being the same. The product was isolated in the same way. Yield 45.2 g, 90.6%.

Example 30

Hydrogel formation through oxidation of MBA30-SH-d by hydrogen peroxide (HG-MBA30-f). The same procedure described in Example 15, but substituting MBA30-SH-d for MBA30-SH-a, the other reaction condition being the same. The product was isolated in the same way. Yield 46.2 g, 92.6%.

Example 31

Hydrogel formation through oxidation of BP30-SH-d by the air oxygen (HG-BP30-d). The same procedure described in Example 14, but substituting BP30-SH-d (50 g, 0.043 mol thiol functional groups) for MBA30-SH-a, the other reaction condition being the same. The product was isolated in the same way. Yield 45.6 g, 91.4%.

Example 32

Hydrogel formation through oxidation of BP30-SH-d by hydrogen peroxide (HG-BP30-e). The same procedure described in Example 15, but substituting BP30-SH (50 g, 0.043 mol thiol functional groups) for MBA30-SH, consequently changing the hydrogen peroxide amount (29.2 g, 0.043 mol), the other reaction condition being the same. The product was isolated in the same way. Yield 43.8 g, 87.7%.

Example 33

Hydrogel formation through oxidation of BP50-SH-d by the air oxygen (HG-BP50-e). The same procedure described in Example 14, but substituting BP50-SH (50 g, 0.064 mol thiol functional groups) for MBA30-SH, the other reaction conditions being the same. The product was isolated in the same way. Yield 44.8 g, 89.9%.

Example 34

Hydrogel formation through oxidation of BP50-SH-d by hydrogen peroxide (HG-BP50-f). The same procedure described in Example 15, but substituting BP50-SH (50 g, 0.064 mol thiol functional groups) for MBA30-SH, consequently changing the hydrogen peroxide amount (43.36 g, 0.064 mol), and the amount of TRIS buffer (20 ml), the other reaction condition being the same. The product was isolated in the same way. Yield 44.1 g, 88.5%.

Example 35

Examples 10, 12 can be duplicated as follows. The same procedure as in Example 10 or 12 can be followed, by substituting 5,5-dithiobis(2-nitrobenzoic acid), the formula of which is shown below, for an equimolecular amount of 2,2'-dipyridyldisulphide, the other conditions being equal.

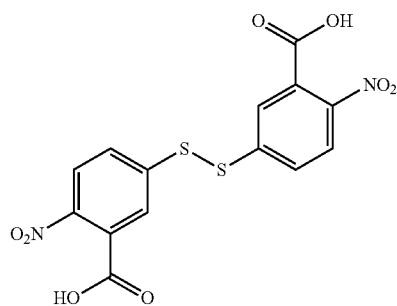 [SMILES: O=C(O)c1cc(SSc2ccc([N+](=O)[O-])c(C(=O)O)c2)ccc1[N+](=O)[O-]]

5,5'-dithiobis(2-nitrobenzoic acid)

The resultant product contains thio(2-nitrobenzoic acid) moieties in place of 2-pyridysulphide moieties. Its reactivity towards thiol-exchange reactions is the same.

Materials and Methods

Materials (L)-Cysteine (>99.0%), potassium carbonate (99%), 1,4-dithio-D,Lthreitol (99%) were purchased from Fluka and used without further purification. $D_2O$ (99.9%) stabilised over silver coil, 2,2-methylenebisacrylamide (henceforth called MBA) 1,4-(D,L)-dithiotreitol (henceforth called DTT), sodium metabisulfite ($Na_2S_2O_5$) bi-pyridyidisulphide, tris-hydroxymethylaminomethane (henceforth called TRIS) and 2-methylpiperazine (henceforth called MP) were purchased from Aldrich.

Standard HCl aqueous solutions were purchased from Rieden de Haen. 2,2-bis(acrylamido)acetic acid (henceforth called BAC), bis(acryloyl)piperazine (henceforth called BP) and N-tert-Butyloxycarbonyl cystamine were synthesised as previously described (Ferruti, P.; Ranucci, E.; Trotta, F.; Gianasi, E.; Evagorou, G. E.; Wasil, M.; Wilson, G.; Duncan, R. Macromol. Chem. Phys. 1999, 200, 1644; Ferruti, P. *Macromol. Synth.* 1985, 9, 25 and K. A. Jacobson, B. Fischer, X. Ji, *Bioconjugate Chem.* 1995, 6, 255).

Instruments and Methods.

The $^1H$ and $^{13}C$ spectra were acquired on a Brüker Avance 400 spectrometer, operating at 500.133 MHz ($^1H$) and at 125.00 MHz ($^{13}C$). Size exclusion chromatography (SEC) traces were obtained making use of TSK-gel G4000 PW and TSK-gel G3000 PW columns produced by TosoHaas. The two columns were connected in series and the mobile phase was Tris buffer pH 8,10; flow rate 1 mL/min (Waters model HPLC pump 515); the UV detector was a Waters model 486, operating at 230 nm; the refractive detector was a Waters model 2410. The samples were prepared in Tris buffer with a 1% concentration in polymer. Molecular weight determinations were based on a calibration curve obtained with pullulan standards.

Summary and Conclusions

Using these examples, the inventors have shown that PAAs can be produced containing cystamine residues which are BOC protected using two different pairs of co-monomers and different levels of cystamine incorporation. All of these different polymers can be reduced to give a free sulphydryl group by using either dithiothreitol or sodium metabisulphite as the reductant. Activated polymers containing bipyridyidisulphide have been produced by a thiol disulphide interchange reaction using polymers produced by either of the PAAs with different co-monomers.

The inventors have further shown that hydrogels may be prepared from these cystamine containing polymers by a number of routes These routes are (1) by admixture of polymers containing a free sulphydryl group and polymers containing a pyridyl disulphide activated polymers, or (2) by oxidation using either oxygen in air or hydrogen peroxide. The inventors have also demonstrated that hydrogels may be created in situ by incorporation of unprotected cystamine into the polymerisation reaction, also demonstrated by using two different co-monomer pairs and different quantities of cystamine. Hydrogels prepared by this third route can be reduced to form non-cross-linked polymers using either dithiothreitol or sodium bisulphite as reducing agents. The non-cross-linked polymers produced in this way can be reassembled into hydrogels using either oxygen in air or hydrogen peroxide exactly as freshly prepared polymers.

In conclusion, the inventors note that the polyamidoamines disclosed herein provide a versatile group of polymers which can be synthesised containing a cystamine group. A variety of chemical routes can be used to reduce or activate the polymers to form hydrogels, and the hydrogels can be reduced to their component polymers and reformed. It is expected that this versatile and diverse group of reversibly cross-linkable polymers will therefore find application in a variety of biomedical applications as hydrogels or other applications where cross-linking is beneficial Further Instruments and Methods $^1$H and $^{13}$C NMR spectra were run on a Brüker Advance 400 spectrometer operating at 400.132 MHz ($^1$H) and 100.623 ($^{13}$C). Size exclusion chromatography (SEC) traces of polymers soluble in organic solvents (polystyrene standards) were obtained using Phenomenex Phenogel 500, 103, and 104 A columns, connected in series, equipped with a UV detector operating at 254 nm, mobile phase 9/1 (v/v) dichloromethane/methanol. SEC traces of water soluble polymer (pullulan standards) were obtained using a WATERS 515 HPLC PUMP instrument, with Toso-Haas 486 columns, using 0.1 M Tris buffer pH 8.00±0.05 as mobile phase equipped with a Light Scattering Viscotek 270 dual detector and a RI Waters 2410 detector.

Materials

Tris-(hydroxymethyl)-aminomethane (TRIS) (>99.8%), 2-mercaptopyridine (>95%), lithium hydroxide monohydrate (>98%) and cystamine di-hydrochloride (>98%), poly(ethylene glycol) methyl ether 750, poly(ethylene glycol) methyl ether 2000, carbonyl di-imidazole (>97%), piperazine (>99%), morpholine (>99%), N,N'-methylenebis(acrylamide) (>98%), N,N'-dimethylethylenediamine (>98%), di-tert-butyl-dicarbonate (>98%), were purchased from Fluka and used as received. Analytical grade HPLC solvents were purchased from Fluka and used as received. D$_2$O (99.9%), d$_6$-DMSO (99.8%), CDCl$_3$ (99.8%), 2,2'-dithiodipyridine (98%) was purchased from Aldrich and used as received. Water was distilled twice.

Example 36

Homo Poly(MBA-DMEDA), 30K, Morpholine Terminated (MBA-DMEDA30)

For the compound MBA-DMEDA30, "A30" refers to the approximate Mn of the polymer.

MBA (1.54 g, 10.0 mmol) was added in small portions to an aqueous solution of DMEDA (0.88 g, 10.0 mmol in 3.5 ml of water) under nitrogen. The reactive solution was allowed to react for 72 hours under stirring, then morpholine (87.5 □l, 1.0 mmol) was added and allowed to react for 24 hours. Subsequently the pH was adjusted to 2.5 with a 1 M aqueous HCl, the solution was ultrafiltered through a membrane with a molecular weight cut off 3,000 and freeze dried.

Product was characterized by SEC and NMR spectroscopy.

$^1$H NMR (d$_6$-DMSO): 2.25 (s, 6H, CH$_3$N); 2.39 (t, 4H, CO—CH$_2$—CH$_2$—N); 2.51 (s, 4H, N—CH$_2$—CH$_2$—N); 2.66 (t, 4H, CO—CH$_2$—); 4.56 (m, broad, 2H, NH—CH$_2$—NH), 8.82 (t, broad, 2H, NH).

$\overline{M}_n$: 27000, $\overline{M}_w$: 42000; Yield: 2.6 g, 93%.

Example 37

Homo Poly(MBA-DMEDA), 5K, Amino Terminated (Scheme 1/B)(MBA-DMEDA5)

The same procedure described in Example 36 was followed, but using a different amount of DMEDA (0.924 g, 10.5 mmol), the quantities of the other reagents being the same. The crude product was diluted with water and lyophilized without any further purification.

Yield: quantitative. $\overline{M}_n$: 3800; $\overline{M}_w$: 7900

NMR spectrum similar to the one obtained with the product of Example 36

Example 38

Homo Poly(MBA-DMEDA), 10K, Amino Terminated (Scheme 1/B)(MBA-DMEDA10)

The same procedure described in Example 36 was followed, but using a different amount of DMEDA (0.902 g, 10.25 mmol), the quantities of the other reagents being the same. The crude product was diluted with water and lyophilized without any further purification.

Yield: quantitative. $\overline{M}_n$: 11600; $\overline{M}_w$: 28000

NMR spectrum similar to the one obtained for the product of Example 36.

Example 39

N-tert-Butyloxycarbonyl Cystamine Hydrochloride (Cyst-mBoc.*HCl)

TEA (2.696 g, 26.65 mmol) was added to a dry methanol solution (100 ml) of cystamine bis-hydrochloride (2.00 g, 8.88 mmol), and the solution was stirred for 15 min at room temperature. Di-tert-butyidicarbonate (1.941 g, 8.88 mmol) was added and the reaction was stirred for an additional 2.5 h, monitoring the reaction progress by TLC (eluent: chloroform/isopropyl alcohol 1:1, Rf product: 0.25). The solvent was then evaporated, and a 1 M KH$_2$PO$_4$ aqueous solution (60 ml, pH=4.2) was added. The aqueous phase was extracted with diethyl ether (50 ml) to remove N,N'-di-tert-butyloxycarbonyl cystamine, then brought to pH 9 with 1 M NaOH, and extracted with ethyl acetate (6×15 ml). The combined organic phases were dried (Na$_2$SO$_4$) and evaporated to dryness. The residue was dissolved in water at pH 4 (HCl). The clear solution obtained was freeze-dried and N-tert-butyloxycarbonyl-cystamine isolated as hydrochloride (1.03 g, 40%).

$^1$H NMR (D$_2$O): 1.30 (s, 9H, Boc CH$_3$), 2.72 (t, 2H, CH$_2$—S), 2.83 (t, 2H, CH$_2$—S), 3.21-3.31 (m, 4H, NH$_3^+$—CH$_2$ and CONH—CH$_2$).

Example 40

Mono-piperazine Terminated Mono-methoxy-PEG2000 (PEG2000-NH)

Referring to Scheme 10A, in a two necked round bottom flask equipped with stirring bar, vacuum/nitrogen inlet and a glass stopper, mono-methoxy-PEG 2000 (5 mmol, 10 g) was softened under gentle warming, purged and kept under nitrogen. CHCl$_3$ (50 mL) was added allowing to dissolve PEG and CDI (15 mmol, 2.4 g) was subsequently added in small portions. After 1 hour, unreacted CDI was quenched by addition of water (5 ml) and the organic phase was extracted with brine (4×30 ml). The organic phase was dried over anhydrous sodium sulphate, piperazine (1.3 g, 15 mmol) was added and the solution was left stirring for 1 hour. The organic solution was extracted with brine until the washing liquor reached a neutral pH. It was subsequently dried over anhydrous sodium sulphate and the solvent evaporated under reduced pressure. The crude pale yellow oily product was kept under vacuum for several days until a waxy substance was obtained in quantitative yield.

$^1$H NMR (D$_2$O): 2.71 (t, broad, 4H, CH$_2$—NH—CH$_2$, piperazine), 3.30 (s, 3H, O—CH$_3$, PEG terminus), 3.38 (broad, 4H, CH$_2$—N(CO)—CH$_2$, piperazine), 3.5-3.8 (m, broad, 70 H, CH$_2$O—CH$_2$, PEG chain), 4.17 (broad, 2H, CO—O—CH$_2$, PEG).

Example 41

Mono-piperazine Terminated Mono-methoxy-PEG750 (PEG750-NH)

Referring to Scheme 10A, the same procedure described in Example 40 was followed, but using a mono-methoxy PEG with a different chain length in the same molar amount (5 mmol, 3.27g), the quantities of the other reagents being the same. The product was isolated in the same way.

$^1$H NMR (D$_2$O): 2.71 (t, broad, 4H, CH$_2$—NH—CH$_2$, piperazine), 3.30 (s, 3H, O—CH$_3$, PEG terminus), 3.38 (broad, 4H, CH$_2$—N(CO)—CH$_2$, piperazine), 3.5-3.8 (m, broad, 70 H, CH$_2$O—CH$_2$, PEG chain), 4.17 (broad, 2H, CO—O—CH$_2$, PEG).

Example 42

CP03 (CP16-4-15)

Referring to Scheme 10C and Scheme 11, and FIG. 19, for the compound CP16-4-15), "CP" means "Complexing Polymer", and the numbers refer to the average number of the repeating units of the PEG terminus, the SH containing part, and the homo-MBA-DMEDA part, respectively. Therefore, for CP03, the Complexing Polymer has 16 repeating units of the PEG terminus, 4 repeating units for the SH containing part, and 15 repeating units for the homo-MBA-DMEDA part.

In a two-necked flask, MBA (0.308 g, 2.0 mmol), the product obtained in example 4 (0.460 g, 1.6 mmol) and TEA (0.160 g, 0.220 mL, 1.6 mmol) were dissolved in ethylene glycol (2 mL) under nitrogen flow. The reaction was monitored by TLC (eluent: chloroform/ isopropyl alcohol 1:1, Cyst-mBoc Rf: 0.25). After the reaction was complete, the product obtained in Example 41 (0.152 g, 0.2 mmol) diluted in ethylene glycol (0.5 ml) was added. The mixture was allowed to react for 5 days. Finally the product obtained in Example 37 (0.5 g, 0.2 mmol) diluted in ethylene glycol (2 ml) was added and the mixture was allowed to react for 5 days. After the reaction was complete the mixture was diluted in water (100 ml), a 1 M HCl aqueous solution was added until pH 4 was reached and the final solution dialysed against water (5×1 L) in a 3,500 nominal cut off dialysis tube. The purified product was eventually lyophilized. Yield: 52%

$^1$H NMR (D$_2$O): 1,41 (s, O—C—(CH$_3$)$_3$, cyst-m-Boc), 2,57 (s, N—CH$_3$, PAA-block), 2,61 (m, CO—CH$_2$—CH$_2$—N, PAA-block), 3,07 (s, N—CH$_2$—CH$_2$—N, PAA-block), 3,11 (m, CO—CH$_2$—CH$_2$—N, PAA-block), 3,67 (s, O—CH$_2$—CH$_2$—O, PEG-block), 4.57 (s, NH—CH$_2$—NH, PAA-block), 6.22 (d, CH=CH$_2$, terminus)

Integral ratios between NMR peak integrals are as expected. A reaction yield of 72% is calculated on the basis of the signal referred to the unreacted double bond (6.22 ppm).

Example 43

CP04 (CP16-4-48)

For CP04, the Complexing Polymer has 16 repeating units of the PEG terminus, 4 repeating units for the SH containing part, and 48 repeating units for the homo-MBA-DMEDA part.

Referring to FIG. 19, the same procedure described in Example 42 was followed, but using the product obtained in Example 38 (1.0 g, 0.2 mmol) instead of the product obtained in Example 37, the quantities of the other reagents being the same. The product was isolated in the same way. Yield: 54%. NMR spectrum was similar to the one obtained for the product of Example 42. Integral ratios between NMR peak integrals are as expected. Reaction yield of 70%.

Example 44

CP05 (CP45-4-15)

Therefore, for CP05, the Complexing Polymer has 45 repeating units of the PEG terminus, 4 repeating units for the SH containing part, and 15 repeating units for the homo-MBA-DMEDA part.

Referring to FIG. 19, the same procedure described in Example 42 was followed, but using the product obtained in Example 40 (0.4 g, 0.2 mmol) instead of the product obtained in Example 41, the quantities of the other reagents being the same. The product was isolated in the same way. Yield: 53%. NMR spectrum was similar to the one obtained for product of Example 42. Integral ratios between NMR peak integrals are as expected. Reaction yield of 68%.

Example 45

CP06 (CP45-4-48)

Therefore, for CP03, the Complexing Polymer has 45 repeating units of the PEG terminus, 4 repeating units for the SH containing part, and 48 repeating units for the homo-MBA-DMEDA part.

Referring to FIG. 19, the same procedure described in Example 44 was followed, but using the product obtained in Example 38 (1.0 g, 0.2 mmol) instead of the product obtained in Example 37, the quantities of the other reagents being the same. The product was isolated in the same way. Yield: 56%. NMR spectrum was similar to the one obtained for the product of Example 42. Integral ratios between NMR signals are as expected. Reaction yield of 65% is calculated on the basis of the peak integrals referred to the unreacted double bond (6.22 ppm).

Example 46

(XLP-30K, XLP-10K, XLP-5K, XLP-3K, XLP-1K) (MBA-Py25-110, MBA-Py25-35, MBA-Py25-20, MBA-Py25-10, MBA-Py25-4)

Referring to Scheme 12, for each label: Py25 refer to the molar content of Py groups on the repeating units, the second number refers to the average number of repeating units in the polymer chains.

Polymerisation of MBA with DMEDA and Cystamine (30%) (HG-MBA30-g).

In a round bottomed flask, equipped with a magnetic stirrer and nitrogen inlet, MBA (100.2 g, 0.65 mol) was dissolved under inert atmosphere in distilled water (200 mL). Cystamine bis-hydrochloride (22.0 g, 0.0975 mol) was added with the stoichiometric amount of lithium hydroxyde monohydrate (8.18 g, 0.195 mol). When dissolution was complete, DMEDA (40.1 g, 0.455 mol) was added, stirred for half an hour, and allowed to react non-stirred, protected from direct light. After 120 hours a transparent gel was formed, similar in consistency and aspect to HG-MBA30-a as obtained in Example 11. The hydrogel was ground, washed with 0.1 M HCl and several times with distilled water till the washing liquors appeared neutral. The hydrogel was then washed three times with acetone and dried under vacuum to obtain a fine powder. Yield 46.3 g, 92,7%.

Reduction and Dissolution of HG-MBA30-g with DTT (MBA30-SH-e).

In a round bottomed flask, equipped with a magnetic stirrer and nitrogen inlet, HG-MBA30-d (100 g, 0.049 mol of cystamine groups) was allowed to swell under inert atmosphere in distilled water (500 mL). The pH was adjusted to 8.5 with NaOH and a three-fold excess of DTT was added (22.45 g, 0.15 mmol). The solution was allowed to react for 6 hours. It was diluted with a 1.0 M HCl aqueous solution down to pH 2, ultrafiltered through a membrane of 5,000 nominal cut-off in de-oxygenated water, and finally lyophilized. The product was isolated as hydrochloride salt and stored under nitrogen atmosphere. Yield 71.8 g (71.8%). $\overline{M}_n$: 29000; $\overline{M}_w$: 56000

Thiol-disulphide Exchange Between MBA30-SH-e and Bi-pyridyldisulphide (MBA30-Py-b).

In a round bottom flask, equipped with a magnetic stirrer and nitrogen inlet, MBA30-SH (50 g, 0.043 mol thiol functional groups) was dissolved under inert atmosphere in de-oxygenated TRIS buffer (100 mL, 0.1 M, pH 8.5). Bi-pyridyl disulphide (10.4 g, 0.047 mol) was added to the stirred solution, that became almost immediately yellow, due to the presence of 2-mercaptopyridine, and allowed to react for 15 hours. Subsequently the solution was diluted with a 1.0 M HCl aqueous solution down to pH 3.0, fractioned by ultrafiltration through 30,000; 10,000; 5,000; 3,000; 1,000 molecular weight cut off membranes. Each fraction was lyophilized separately.

$^1$H NMR (D$_2$O): 2,71 (m, CO—CH$_2$—CH$_2$—N), 2.77 (s, N—CH$_3$), 3.35 (m, CO—CH$_2$—CH$_2$—N), 3.46 (s, N—CH$_2$—CH$_2$—N), 4.57 (s, NH—CH$_2$—NH), 7.27 (m, pyridine, N—CH—CH), 7.67-7-77 (m, pyridine, N—C—CH—CH), 8.38 (m, pyridine, N—CH—CH)

XLP-30K: yield: 4.3 g; XLP-10K: yield: 3.6 g; XLP-5K: yield: 10.2 .g; XLP-3K: yield: 4.7 g; XLP-1K: yield: 13.7 g. Total yield: 67%. Reaction yield: 83%.

Example 47

Reduction of CP06 with DTT

Reduction of PEG-MBA/DMEDA16-Cys-PEG with DTT (PEG-MBA/DMEDA16-SH-PEG). In a round bottom flask, equipped with a magnetic stirrer and nitrogen inlet, PEG-MBA/DMEDA16-Cys (250 mg, 0.013 mmol) was dissolved under inert atmosphere in distilled water (10 mL). pH was adjusted to 8.5 with NaOH and a ten-fold excess of DTT was added (160mg, 0.104 mmol). The reactive solution was allowed to react for 1 hour. It was diluted with 1.0 M HCl aqueous solution down to pH 2, ultrafiltered through a membrane of 5,000 nominal cut-off using de-oxygenated water and lyophilized. The product was isolated as hydrochloride salt and stored under nitrogen atmosphere.

Example 48

Making of Complexes

The interaction between polyamidoamines and DNA has been characterised using crude salmon sperm DNA (ssDNA) that has been cleaned up and fractionated to give a preparation of mainly single stranded DNA molecules.

ssDNA (2.5 μg) was mixed at different ratios with polymers to form a DNA polycation complex (DNA:PAA, 1:1, 1.25:1, 1.5:1 and 2:1). The ratio is calculated by DNA bases per monomer of the polymer. Also the ratio of MBA/DMEDA25-Py to PEG-MBA/DMEDA16-SH-PEG has been varied (ie 2:1 and 3:1).

Furthermore, the order of addition of reagents was also investigated. Three different methods listed below were used in which the order of adding the components was varied:

(1) add MBA/DMEDA25-Py (small volume, 20 μl) to DNA (2.5 μg in 50 μl), then add PEG-MBA/DMEDA16-SH-PEG to complex;

(2) add MBA/DMEDA25-Py (big volume, 30 μ) to DNA (2.5 μg in 50 μl), then add PEG-MBA/DMEDA16-SH-PEG to complex; and (3) add MBA/DMEDA25-Py (big volume, 30 μl) to PEG-MBA/DMEDA16-SH-PEG (20 μl), then add polymers to DNA (2.5 μg in 50 μl).

The sizes of carrier particles comprising PAA and DNA, under various conditions (ie which preparation method was used, and what ratio was used) have been assessed using Dynamic Light Scattering (DLS), and the results are shown in FIGS. 13 and 14.

Using the 3$^{rd}$ method, all particles sizes are comparable, while some variation is observed for the 1$^{st}$ method at low PAA:DNA ratios. The size, employing the 2$^{nd}$ method using a 2:1 MBA/DMEDA25-Py to PEG-MBA/DMEDA16-SH-PEG ratio and a 1:1 PAA: DNA ratio, is smaller than the 3:1 formulation. Small particle sizes can be obtained using a cross-linked formulation and are in a suitable range for biomedical or environmental applications.

Representative Transmission Electron Microscopy (TEM) images of complexes produced with a 2:1 MBA/DMEDA25-Py to PEG-MBA/DMEDA16-SH-PEG ratio and a 1.25:1 PAA:DNA ratio, and with a 3:1 MBA/DMEDA25-Py to PEG-MBA/DMEDA16-SH-PEG ratio and a 1.25:1 PAA: DNA ratio are shown in FIG. 15. Toroidal shaped particles were formed having a size of 35 nm and 20 nm, respectively.

TEM method: One drop of each sample was placed onto copper grids coated with Pioloform resin (Taab Laboratory Equipment, Reading, UK) and excess liquid blotted using filter paper. After air drying, the grids were floated on a drop of uranyl acetate staining solution (4% w/v in 50/50 v/v EtOH/H$_2$O) for 15 min, after which they were washed once in 50% v/v EtOh and twice in purified water, followed by air drying. Grids were analyzed using a JEOL JEM-1010 transmission electron microscope (Jeol, Welwyn Garden City, UK) operating at a voltage of 80 kV. Micrographs were taken at various magnifications with a Kodak Megaplus digital camera 1.6i using the Analysis 3.0 software package.

Example 49

Behaviour of Complexes in the Presence of Sodium Sulphate

The stability of the complexes in different salt concentrations was investigated. Complexes were made as described before using the 3$^{rd}$ method. Then either water, 1 mM sodium sulphate or 10 mM sodium sulphate were added to the complexes and sizes were measured using DLS. As seen in FIGS. 15 and 16 complexes made using a 2:1 MBA/DMEDA25-Py to PEG-MBA/DMEDA16-SH-PEG ratio are more stable (smaller particles sizes) to sodium sulphate than the 3:1 formulation.

Example 50

Cross-linked Formulations

Cross-linked formulations were compared to their non cross-linked state. Complexes were placed on top of a centrifugal ultrafilter (cut off Mwt: 100 kDa, Microcon YM-100, Amicon, Fischer Scientific, Loughborough, UK), and spun at 1000 g for 30 min. TEM images were taken of the filtrate and what remained on the filter.

FIG. 18 shows more complexes on filter for cross-linked formulation (top pictures) compared to non-cross-linked system (bottom pictures), and less went through filter for cross-linked formulation (top) compared to non-cross-linked (bottom). This is proof that the physical cross-linking took place.

The invention claimed is:

1. A composition comprising linear polyamidoamine (PAA) polymer chains, each chain comprising a pendant disulphide, sulphydryl, or activated sulphydryl moiety, wherein the linear PAA polymer chains under oxidizing conditions form disulfide cross-links to produce a cross-linked product, and wherein the cross-linked product is reducible to break cross-links between the polymer chains.

2. A composition according to claim 1, wherein the PAA polymer contains repeating groups X and Y represented by the general formula I:

$$\{-[X]-[Y]-\}_n \quad \text{(Formula I)}$$

in which, n is between 5 and 500;

the groups X, which may be the same or different, are amide-containing groups of the formula $$-[-L^1-CO-NR^1-L^2-NR^2-CO-L^3-]-$$

wherein $L^1$ and $L^3$ independently represent optionally substituted ethylene groups;

$L^2$ represents an optionally substituted alkylene chain; and $R^1$ and $R^2$ independently represent hydrogen or an optionally substituted alkyl group;

and the groups Y, which may be the same or different, represent amine-derived groups of the formula:

$$-[-NR^3-]- \text{ or } -[-NR^4-L^4-NR^5-]-$$

wherein $R^3$, $R^4$ and $R^5$ represent optionally substituted alkyl groups, and $L^4$ represents an optionally substituted alkylene group;

or $R^4$, $R^5$ and $L^4$, together with the nitrogen atoms to which they are attached, form an optionally substituted ring, with the proviso that at least some of $R^3$, $R^4$ and $R^5$ contain disulphide, sulphydryl or activated sulphydryl groups.

3. A composition according to claim 2, wherein $R^1$ and $R^2$ are hydrogen.

4. A composition according to claim 2, wherein where $R^1$ and/or $R^2$ represents an optionally substituted alkyl group containing a $C_1$-$C_{20}$ chain.

5. A composition according to claim 2, wherein $R^3$, $R^4$ and $R^5$ represent optionally substituted alkyl groups containing a $C_1$-$C_{20}$ chain.

6. A composition according to claim 2, wherein $L^2$ and $L^4$ represent optionally substituted alkylene chains containing 1-10 carbon atoms.

7. A composition according to claim 2, wherein where any of $L^1$, $L^2$, $L^3$ and $L^4$ are substituted, the substituents are selected from alkyl, alkoxy, acyl, acylamino, carboxy, cyano, halo, hydroxy, nitro, trifluoromethyl and amino.

8. A composition according to claim 2, wherein at least some of $R^3$, $R^4$ and $R^5$ are substituted by groups selected from sulphydryl, activated sulphydryl and $-S-S-R^6$, wherein $R^6$ represents alkyl optionally substituted by one or more substituents selected from alkyl, alkoxy, acyl, acylamino, carboxy, cyano, halo, hydroxy, nitro, trifluoromethyl and amino.

9. A composition according to claim 2, wherein in Formula I, n is between 20 and 100.

10. A composition according to claim 2, wherein the Molecular Weight of the PAA polymer is between 1500 Da and 120,000 Da.

11. A composition according to claim 2 wherein the composition further comprises PEG, whereby the cross-linked product is a copolymer 12. A method of preparing the composition of claim 1 comprising: reacting a bisacryloyl compound with a primary amine and/or a secondary di-amine, one or both of which contains a disulphide group.

13. A method according to claim 12, wherein the bisacryloyl compound used in the method has the formula II:

$$CH_2=CH-CO-NR^1-L^2-NR^2-CO-CH=CH_2 \quad \text{(Formula II)}$$

wherein $R^1$, $R^2$, and $L^2$ are as defined in relation to Formula I.

14. A method according to claim 13, wherein $R^1$ and $R^2$ are hydrogen.

15. A method according to claim 13, wherein $L^2$ is a $CH_2$ group.

16. A method according to claim 12, wherein the bisacryloyl compound is methylene bisacrylamide (MBA).

17. A method according to claim 12, wherein when a primary amine containing a disulphide is used, the primary amine containing a disulphide group has the formula III:

$$NH_2-R^3 \quad \text{(Formula III)}$$

wherein $R^3$ is as defined in Formula I.

18. A method according to claim 17, wherein $R^3$ represents an alkyl group substituted by -S-S-$R^6$, wherein $R^6$ is alkyl optionally substituted by one or more substituents selected from alkyl, alkoxy, acyl, acylamino, carboxy, cyano, halo, hydroxy, nitro, trifluoromethyl and amino.

19. A method according to claim 12, wherein the primary amine containing a disulphide group is cystamine, which may be unprotected.

20. A method according to claim 12, wherein the primary amine is cystamine, one amine group of which carries a protecting group.

21. A method according to claim 12, wherein when a secondary di-amine containing a disulphide is used, the secondary di-amine has formula IV:

$$H-NR^4-L^4-NR^5-H \quad \text{(Formula IV)}$$

wherein $R^4$, $R^5$ and $L^4$ are as defined in relation to Formula I.

22. A method according to claim 21, wherein $R^4$ or $R^5$ represent an alkyl group substituted by -S-S-$R^6$, wherein $R^6$ is alkyl optionally substituted by one or more substituents selected from alkyl, alkoxy, acyl, acylamino, carboxy, cyano, halo, hydroxy, nitro, trifluoromethyl and amino.

23. A method according to claim 12, wherein the method involves the use of amine molecules that do not contain any disulphide groups.

24. A method according to claim 12, wherein the secondary di-amine has formula V:

$$CH_3-NH-CH_2-CH_2-NH-CH_3 \quad \text{(Formula V)}.$$

25. A method according to claim 12, wherein the secondary di-amine is either dimethylethylenediamine (DMEDA), or 2-methyl-piperazine.

26. A method according to claim 12, wherein the method comprises reacting a bisacryloyl compound of Formula II, with a primary amine containing a disulphide group of Formula III, with a secondary di-amine of Formula V.

27. A hydrogel comprising a plurality of linear polyamidoamine (PAA) polymer chains that are cross-linked via linking groups containing reducible disulphide bonds.

28. A hydrogel according to claim 27 wherein the cross-links between PAA polymer chains are broken when the hydrogel is reduced.

29. A hydrogel according to claim 28, wherein the cross-linked PAA hydrogel is reducible upon contacting with a reducing agent selected from the group consisting of dithiothreitol (DTT), sodium metabisulphite, and glutathione.

30. A method of preparing a hydrogel comprising a plurality of polyamidoamine (PAA) polymer chains of claim 1 that are cross-linked via linking groups containing reducible disulphide bonds, the method comprising: (i) reacting a bisacryloyl compound with a primary amine and/or a secondary di-amine, one or both of which contains a disulphide group, to form PAA polymer chains, and (ii) allowing reducible disulphide bonds to form between the PAA polymer chains.

31. A method for preparing a composition comprising a copolymer of polyethylene glycol (PEG) and polyamidoamine (PAA) comprising a pendant disulphide, sulphydryl, or activated sulphydryl moiety, which may or may not be cross-linked, the method comprising contacting monomers of the linear polyamidoamine (PAA) of claim 1 with amine-terminated PEG; and allowing the corresponding copolymer to form.

32. A delivery composition for delivering a payload molecule, the delivery composition comprising a payload molecule combined with a composition comprising a linear polyamidoamine (PAA) polymer comprising a pendant disulphide, sulphhydryl, or activated sulphydryl moiety, or a hydrogel comprising a plurality of linear polyamidoamine (PAA) polymer chains that are cross-linked via linking groups containing reducible disulphide bonds.

33. A method for preparing the delivery a payload molecule, the delivery composition comprising a pendant disulphide, sulphydryl, or activated sulphydryl moiety, or a hydrogel comprising a plurality of linear polyamidoamine (PAA) polymer chains that are cross-linked via linking groups containing reducible disulphide bonds, to form a mixture, abd exposing the mixture to conditions such that the payload molecule combines with the composition or hydrogel, thereby forming a payload delivery composition according to claim 32.

34. A carrier particle adapted in use to carry a payload molecule to a target site, the carrier particle comprising the composition according to claim 15, wherein the payload molecule is capable of being active when the particle is at least adjacent the target site.

35. A carrier particle according to claim 34, wherein the payload molecule comprises a biologically active compound or biomolecule.

36. A carrier particle according to claim 34, wherein the payload molecule comprises a whole cell, part of a cell, a virus, phage, a micro-organism, an organelle, a virus particle, an amino acid, a peptide, a protein, an enzyme, an antibody, or a polysaccharide.

37. A carrier particle according to claim 34, wherein the payload molecule comprises a nucleic acid or a derivative thereof.

38. A carrier particle according to claim 34, wherein the payload molecule comprises DNA or cDNA or RNA.

39. A carrier particle according to claim 34, wherein the carrier particle is in the size range 10 nm to 500 nm.

40. A carrier particle according to claim 34, wherein the carrier particle comprises PEGylated and non-PEGylated polyamidoamine (PAA).

41. A carrier particle according to claim 34 wherein the PAA-based composition comprises a PEG-PAA-PEG or PEG-PAA copolymer, and a PAA homopolymer, both containing pendant sulphydryl groups.

42. A carrier particle according to claim 34, wherein the ratio of PEG:total PAA is between 1:4 and 1:17.

43. A carrier particle according to claim 34, wherein the ratio of PAA:nucleic acid (NA) is between 0.5:1 and 2.0:1.

44. A carrier particle according to claim 34, wherein the number of pendant disulphide, sulphydryl or activated sulphydryl moieties from the PEG-PAA component is a minimum of six, and wherein the amount of pendant disulphide, sulphydryl or activated sulphydryl moieties in the PAA component is between 0.5 and 2 times that of the PEG-PAA component.

45. A carrier particle according to claim 37, wherein the carrier particle is prepared by reacting PEGylated PAA with non-PEGylated PAA, followed by contacting the resultant composition with the nucleic acid.

46. A fluid tracking system for tracking fluid flow, the system comprising a carrier particle according to claim 34, and detection means for detecting the payload molecule.

47. A method of tracking fluid, the method comprising the steps of:
  (i) applying a carrier particle according to claim 34 comprising a detectable payload molecule to a fluid at a first location; and
  (ii) detecting the payload molecule at a second location of the fluid.

48. A method according to claim , the method comprises a step of isolating the particle from the fluid at the second location prior to detection of the payload molecule with detection means.

49. A method according to claim 47, wherein the method comprises a step of isolating the payload molecule from the carrier particle prior to detection.

50. A method according to claim 34, wherein the isolation step comprises reducing the carrier particle to release the payload molecule prior to detection.

51. A method according to claim 47, wherein the payload molecule comprises nucleic acid, such as DNA, which is detectable by suitable detection means, e.g. PCR.

52. A method according to claim 47, wherein the payload molecule comprises a single stranded oligonucleotide.

53. A method according to claim 47, wherein the payload molecule comprises a carrier compound, which may be carrier DNA.

54. A method according to claim 53, wherein the carrier DNA is degraded to give a preparation of mainly single stranded DNA molecules of mixed sequence with approximately the same size as the detection nucleic acid.

55. A cell-supporting medium comprising a composition of claim 1

56. A method of preparing a cell-supporting medium according to Claim 55, the method comprising the steps of:
  (i) contacting a composition comprising a polyamidoamine (PAA) polymer comprising a pendant disulphide, sulphydryl, or activated sulphydryl moiety, or a hydrogel comprising a plurality of polyamidoamine (PAA)

polymer chains that are cross-linked via linking groups containing reducible disulphide bonds with at least one cell; and (ii) exposing the hydrogel or composition to conditions such that the at least one cell is supported thereon or therein, thereby forming a cell-supporting medium.

57. A pharmaceutical composition comprising a therapeutically effective amount of a composition according to claim 1 and a pharmaceutically acceptable excipient.

58. A method of treatment of a medical condition characterised by tissue loss or damage, wherein said method comprises administration to a subject of an effective amount of a composition according to claim 1.

59. A method according to claim 58, wherein the condition characterised by tissue loss or damage includes the treatment of wounds, tissue degenerative disorders and loss of tissue function.

60. A method according to claim 59, wherein the tissue degenerative disorders include neurodegenerative disorders, intervertebral disc disorders, cartilage or bone degeneration, liver degenerative disorders, kidney degenerative disorders, muscle atrophy, and nerve damage or loss.

61. A cell supporting medium comprising a hydrogel of claim 27 and at least one cell.

62. A pharmaceutical composition comprising a hydrogel of claim 27 and a pharmaceutically acceptable excipient.

* * * * *